(12) United States Patent
Cremer et al.

(10) Patent No.: US 7,976,585 B2
(45) Date of Patent: Jul. 12, 2011

(54) POLYMERIC DYES

(75) Inventors: Christian Cremer, Lörrach (DE);
Richard Lewis Riggs, Mannheim (DE);
Beate Fröhling, Grenzach-Wyhlen (DE);
Martin Müller, Lörrach (DE)

(73) Assignee: BASF SE Ludwigshafen (DE)

( * ) Notice: Subject to any disclaimer, the term of this patent is extended or adjusted under 35 U.S.C. 154(b) by 0 days.

(21) Appl. No.: 12/598,494

(22) PCT Filed: Apr. 25, 2008

(86) PCT No.: PCT/EP2008/055038
§ 371 (c)(1),
(2), (4) Date: Mar. 5, 2010

(87) PCT Pub. No.: WO2008/138726
PCT Pub. Date: Nov. 20, 2008

(65) Prior Publication Data
US 2010/0192312 A1 Aug. 5, 2010

(30) Foreign Application Priority Data

May 11, 2007 (EP) .................................. 07108002

(51) Int. Cl.
*A61Q 5/10* (2006.01)
*C07F 7/18* (2006.01)
(52) U.S. Cl. .......... 8/405; 8/552; 8/647; 8/657; 556/455
(58) Field of Classification Search ............... 8/405, 552, 8/647, 657; 556/455
See application file for complete search history.

(56) References Cited

U.S. PATENT DOCUMENTS

| | | | |
|---|---|---|---|
| 3,257,330 A | 6/1966 | Burzynski | |
| 4,381,260 A | 4/1983 | Chu | |
| 5,176,906 A | 1/1993 | Lamb | |
| 5,254,655 A | 10/1993 | Gibbons | |
| 6,027,537 A | 2/2000 | Leduc | |
| 6,176,885 B1 * | 1/2001 | Leduc et al. | 8/405 |
| 6,194,534 B1 | 2/2001 | Baumann | |
| 2003/0072728 A1 | 4/2003 | Soane | |
| 2003/0078359 A1 | 4/2003 | Ichinohe | |
| 2003/0226218 A1 | 12/2003 | Richard | |
| 2004/0202623 A1 | 10/2004 | Quadir | |
| 2005/0054797 A1 | 3/2005 | Lai | |
| 2007/0204412 A1 | 9/2007 | Arkles | |
| 2009/0054649 A1 | 2/2009 | Shimada et al. | |
| 2009/0076198 A1 | 3/2009 | Giesenberg | |
| 2009/0099282 A1 | 4/2009 | Muller et al. | |
| 2009/0100610 A1 | 4/2009 | Cremer | |
| 2009/0130045 A1 | 5/2009 | Cremer | |
| 2009/0151091 A1 | 6/2009 | Cremer | |
| 2009/0217465 A1 | 9/2009 | Cremer | |
| 2009/0229059 A1 | 9/2009 | Cremer | |
| 2009/0255063 A1 | 10/2009 | Marquais-Bienewald | |

FOREIGN PATENT DOCUMENTS

| | | |
|---|---|---|
| CN | 1887937 A | 1/2007 |
| EP | 1293541 A2 | 3/2003 |
| WO | 2006125736 A1 | 11/2006 |
| WO | 2007034861 A1 | 3/2007 |

OTHER PUBLICATIONS

STIC Search Report dated Sep. 23, 2010.*
English language abstract of CN 1887937, (Jan. 2007).
Copending U.S. Appl. No. 12/308,042, filed May 2009.

* cited by examiner

*Primary Examiner* — Eisa B Elhilo
(74) *Attorney, Agent, or Firm* — Shiela A. Loggins

(57) ABSTRACT

A highly crosslinked polysiloxane dye comprising at least 10 Si atoms, including at least one moiety of the formula (I) whose open Si-bonds each are linked to an oxygen atom and open O-bond is linked to a silicon atom in the rest of the polysiloxane, and wherein T is a direct bond or an organic spacer group such as $C_1$-$C_{18}$alkylene, $C_2$-$C_{12}$alkenylene, $C_5$-$C_{10}$cycloalkylene, $C_5$-$C_{10}$arylene, —$C_5$-$C_{10}$arylene-($C_1$-$C_{10}$alkylene)- each of which may be end-capped towards the linkage to Dye by CO, COO, $NR^1$, $CONR^1$, $NR^1CONR^1$, CS, CSS, CSNR$^1$, $NR^1CSNR^1$, O, S, SO, $SO_2$, $C_5$-$C_{10}$cycloalkylene, $C_5$-$C_{10}$arylene; or T is $C_3$-$C_{18}$alkylene interrupted, and optionally end-capped towards the linkage to Dye, by CO, COO, $NR^1$, $CONR^1$, $NR^1CONR^1$, CS, CSS, CSNR$^1$, $NR^1CSNR^1$, O, S, SO, —$SO_2$—, $C_5$-$C_{10}$cycloalkylene, $C_5$-$C_{10}$arylene; or is CO; ($CH_2CH_2$—O)$_{1-5}$; COO; N($R^1$); CON($R^1$); O; S; SO; $SO_2$; $R^1$ is hydrogen; unsubstituted or substituted, straight-chain or branched, monocyclic or polycyclic, interrupted or uninterrupted $C_1$-$C_{14}$alkyl; $C_2$-$C_{14}$alkenyl; $C_6$-$C_{10}$aryl; $C_6$-$C_{10}$aryl-$C_1$-$C_{10}$alkyl; or $C_5$-$C_{10}$alkyl($C_5$-$C_{10}$aryl); and Dye is a residue of an organic dye, is useful for dyeing of organic materials, such as keratin-containing fibers, wool, leather, silk, cellulose or polyamides.

(I)

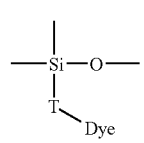

19 Claims, No Drawings

POLYMERIC DYES

The present invention relates to novel polysiloxane dyes in the form of nanoparticles, to compositions comprising these components, to a process for their preparation and to their use for dyeing of organic materials, such as keratin-containing fibers, wool, leather, silk, cellulose or polyamides.

US-2003-072728 proposes physical encapsulation of dye molecules in a polymer shell reactive with the hair.

According to US-2006-112500, keratinic fibers may be died using dyes linked to a monosilane moiety. The preparation of certain chromophor-linked polysiloxanes has been reported in U.S. Pat. Nos. 4,381,260 and 6,194,534. U.S. Pat. Nos. 5,176,906, 6,027,537, 6,176,885 and US-2003-226218 disclose hair dye compositions comprising a linear or cyclic oligosiloxane containing a chrompohor selected from some fluorescent moieties or from neutral quinone, azo or nitrobenzene, bonded to the siloxane chain. Some further silicon-containing azo-dyestuffs are shown in GB-A-2018804.

It has now been found that certain silylated dyes may be converted into highly crosslinked siloxane polymers containing dye moieties, especially cationic dye moieties, and that the polymeric dye particles or pigments thus obtained show advantageous properties especially when applied as dyes for keratinic fibers such as animal or human hair.

The present invention thus pertains to a highly crosslinked polysiloxane containing at least 10 Si atoms and comprising at least one moiety of the formula (I)

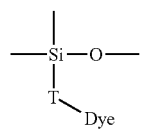

whose open Si-bonds each are linked to an oxygen atom and open O-bond is linked to a silicon atom, thus being part of a crosslinked polysiloxane, and wherein T is a direct bond or an organic spacer group such as $C_1$-$C_{18}$alkylene; $C_2$-$C_{12}$alkenylene; $C_5$-$C_{10}$cycloalkylene; $C_5$-$C_{10}$arylene; —$C_5$-$C_{10}$arylene-($C_1$-$C_{10}$alkylene)-, which may be end-capped towards the linkage to Dye by CO, COO, $NR^1$, $CONR^1$, $NR^1CONR^1$, CS, CSS, $CSNR^1$, $NR^1CSNR^1$, O, S, SO, —$SO_2$—, $C_5$-$C_{10}$cycloalkylene, $C_5$-$C_{10}$arylene; or T is $C_3$-$C_{18}$alkylene interrupted, and optionally end-capped towards the linkage to Dye, by CO, COO, $NR^1$, $CONR^1$, $NR^1CONR^1$, CS, CSS, $CSNR^1$, $NR^1CSNR^1$, O, S, SO, —$SO_2$—, $C_5$-$C_{10}$cycloalkylene, $C_5$-$C_{10}$arylene; or is CO—; —($CH_2CH_2$—O)$_{1-5}$—; COO; $N(R^1)$; $CON(R^1)$; O; S; SO; —$SO_2$—;

$R^1$ is hydrogen; unsubstituted or substituted, straight-chain or branched, monocyclic or polycyclic, interrupted or uninterrupted $C_1$-$C_{14}$alkyl; $C_2$-$C_{14}$alkenyl; $C_6$-$C_{10}$aryl; $C_6$-$C_{10}$aryl-$C_1$-$C_{10}$alkyl; or $C_5$-$C_{10}$alkyl($C_5$-$C_{10}$aryl); and Dye is a residue of an organic dye.

Dye chromophors in the present particles generally are located not only on the particle surface, but in the bulk of the particle. The present dye particles are considerably larger than those of the silsesquioxane type and provide good color intensity and good light fastness, but are still sufficiently small to provide good adhesion to the substrate.

A polysiloxane dye of the invention may be represented by the formula (II)

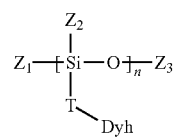

wherein T is as defined above,

Dyh is a residue of an organic dye or a cationic moiety other than the one of an organic dye or is hydrogen;

n, usually denoting the number of silicon atoms in the polysiloxane, is a number from 10 to about $10^9$, preferably from 30 to about $10^8$, especially from about 100 to about $10^7$, while at least 3 moieties Dyh in the polysiloxane of formula (II), especially 10 to 100% of the moieties Dyh in the polysiloxane of formula (II), are a residue of an organic dye;

$Z_1$ and $Z_2$ independently are bonds each linked to an oxygen atom of the rest of the polysiloxane or are OH or alkoxy such as $C_1$-$C_8$alkoxy or halogen;

or $Z_2$ may also be $C_1$-$C_8$alkyl or T-Dyh;

$Z_3$ is a bond linked to a silicon atom of the rest of the polysiloxane or is OH or alkoxy such as $C_1$-$C_8$alkoxy or halogen; or $Z_3$ together with one of $Z_1$ or $Z_2$ commonly form the same chemical bond.

The invention relates to polymeric dye materials whose dimensions, in at least one, especially all 3, spatial direction(s) are in the nanoparticle size range, i.e. usually ranging from 5 to 1000 nm, especially from about 10 to 500 nm, as determined e.g. by dynamic light scattering.

Of special technical interest are globular particles, such as nanoparticles of globular or nearly globular form, wherein the smallest diameter is not less than about 30%, especially about 50%, of the largest diameter.

In preferred polysiloxane dyes of the invention, the number of moieties of the formula (I) ranges from 3 to $10^8$, more preferably from 10 to $10^6$, especially from 15 to 100000. The total number of Si atoms in the polysiloxanes of the invention, depending on the dye loading and the exact type of application, usually ranging from 30 to about $10^9$, preferably from 100 to about $10^8$, especially from about 1000 to about $10^8$; certain particles of specific technical interest contain at least 1000 Si atoms.

Particle sizes are usually determined by dynamic light scattering (DLS). Molecular weights may be determined by field flow fractionation (FFF); in case of small sizes, 20 Si atoms or less, also by mass spectrometry (MS). Molecular weights, numbers of Si units and particle sizes mentioned above or elsewhere in the specification usually are determined by these methods.

Monovalent organic dye moieties known in the art may be used in the present polysiloxanes and precursors for their preparation (shown further below); examples for such dye moieties age given inter alia in US-A-2006-112500 (denoted therein as groups having direct dyeing function; the disclosure of US-A-2006-112500, especially sections [0036] to [0285] therein, being hereby incorporated by reference).

The organic dye moiety Dye is formed from known dyes by abstraction of a hydrogen atom.

A chromophoric moiety Dye usually is a moiety comprising, a dye selected from the group consisting of anthracene dyes, e.g. dyes with an anthracene nucleus not condensed with any other ring, such as hydroxy anthraquinones or ethers or esters thereof; amino anthraquinones or aminohydroxy anthraquinones or ethers or esters thereof, respectively, mercapto-anthraquinones; dyes with anthracene nucleus condensed with one or more carbocyclic rings, such as benzanthrones, perylene derivatives, dibenzanthrones, isodibenzanthrones, pyranthrones, dibenzopyrenequinones, benzanthraquinones, Anthanthrones, benzo-, naphtho-, or anthradianthrones, other dyes in which the anthracene nucleus is condensed with one or more carbocyclic rings; dyes with an anthracene nucleus condensed with one or more heterocyclic rings with or without carbocyclic rings, such as pyrazolanthrones, benzanthronyl-pyrazolanthrone condensation products, dipyrazolanthrones, isothiazolanthrones, isoxazolanthrones, isoselenazolanthrones, thiophenanthrones, benz-azabenzanthrones (anthrapyridones), benzdiazabenzanthrones, e.g. anthrapyrimidones, coeroxenes, coerthienes, coeramidenes, flavanthrones, carbazoles of the anthracene series, anthrimide carbazoles, 1.2 azoles of the anthracene series, 1.3 azoles of the anthracene series, anthraquinone acridones or thioxanthones, amino acridones, compounds containing acridone and carbazole rings, cCondensation products of benzanthronyl-amino anthraquinones, pyridino anthraquinones, azines of the anthracene series, para-diazines, bis-anthraquinonediazines (indanthrones), thiazines, oxazines, cyclic imides or amidines of peri-dicarboxylic acids of the anthracene, benzanthrene, or perylene series; anthracene dyes not provided for above; Indigoid dyes, such as bis-indole indigos, indone-thionaphthene indigos, other indole-indigos, bis-thionaphthene indigos, other thionaphthene indigos; Esters or ester-salts of leuco compounds of vat dyestuffs, e.g. of anthracene dyes or of indigoid dyes; diaryl- or triarylmethane dyes, e.g. derived from diarylmethanes, derived from triarylmethanes, hydroxy derivatives of triarylmethanes in which at least one —OH group is bound to an aryl nucleus, phthaleins, amino derivatives of triarylmethanes without any OH group bound to an aryl nucleus or containing —OH groups bound to an aryl nucleus, phthaleins containing amino groups, triarylmethane dyes in which at least one of the aromatic nuclei is heterocyclic, pyronines;

acridine, azine, oxazine, or thiazine dyes, e.g. acridine dyes; azine dyes of the benzene series, of the naphthalene series or fluorindine or its derivatives; oxazine dyes, such as bisoxazines prepared from amino quinines; thiazine dyes;

quinoline or polymethine dyes, e.g. methine or polymethine dyes, such as cyanine dyes characterised by the methine chain, e.g. cyanines, isocyanines, pseudocyanines, carbocyanines, polycarbocyanines; or containing an even number of ->CH groups, the polymethine chain being branched, e.g. styryl dyes; or the polymethine chain containing hetero atoms; quinophthalones, hydrazone dyes, triazene dyes;

azo dyes, e.g. preparations in which the azo group is formed in any way other than by diazotising and coupling, such as tartrazines; monoazo dyes prepared by diazotising and coupling; disazo or polyazo dyes of the type A→B→C, A→B→C→D, or the like, prepared by diazotising and coupling; disazo or polyazo dyes of the types A→K←B, A→B→K←C, or the like, prepared by diazotising and coupling; disazo or polyazo dyes of the type A←D→B prepared by diazotising and coupling; azo dyes prepared by coupling the diazotised amine with itself; other azo dyes prepared by diazotising and coupling, azo dyes from other azo compounds, azo dyes containing onium groups, azo dyes not provided for in the preceding groups;

porphines or azaporphines, such as phthalocyanines;

quinacridones;

sulfur dyes, e.g. from nitro compounds of the benzene, naphthalene or anthracene series, from amino compounds of the benzene, naphthalene or anthracene series, from azines, oxazines, thiazines, or thiazoles, from urea derivatives, from diphenylamines, indamines, or indophenols or from other compounds;

nitro or nitroso dyes;

quinone imides, such as indamines, indophenols;

azomethine dyes;

azo dyes containing other chromophoric systems, such as azomethine-azo dyes, stilbene-azo dyes, bis- or poly-stilbene-azo dyes, styryl-azo dyes, anthraquinone-azo dyes, phthalocyanine-azo dyes, methine- or polymethine-azo dyes, hydrazone-azo dyes, triazene-azo dyes;

other synthetic dyes of known constitution, such as coumarine dyes, isoindoline dyes, naphtholactam dyes, naphthalimide dyes, phthalimide dyes, perinones, i.e. naphthoylenearyl-imidazoles, benzoxanthene dyes; benzothioxanthene dyes;

dyes of natural origin prepared from natural sources;

and reactive dyes, i.e. dyes which form covalent bonds with the substrates or which polymerise with themselves, especially with the linkage of the reactive group being alternatively specified; with the reactive group directly attached to a heterocyclic ring, the heterocyclic ring being alternatively specified, e.g. to a triazine ring, to a pyridazine ring, to a pyrimidine ring, to a pyrazine ring, to a five-membered ring, to some other heterocyclic ring; with the reactive group not directly attached to a heterocyclic ring; or the reactive group being alternatively specified, the reactive group being an acryloyl group, a quaternised or non-quaternised aminoalkyl carbonyl group, or a (—N)$_n$—CO-A-O—X or (—N)$_n$—CO-A-Hal group, wherein A is an alkylene or alkylidene group, X is hydrogen or an acyl radical of an organic or inorganic acid, Hal is a halogen atom, and n is 0 or 1, the reactive group being a halo-cyclobutyl-carbonyl, halo-cyclobutyl-vinyl-carbonyl, or halo-cyclobutenyl-carbonyl group, the reactive group being an esterified or non-esterified hydroxyalkyl sulfonyl or mercaptoalkyl sulfonyl group, a quaternised or non-quaternised aminoalkyl sulfonyl group, a heterylmercapto alkyl sulfonyl group, a vinyl sulfonyl or a substituted vinyl sulfonyl group, or a thiophene-dioxide group, the reactive group being an esterified or non-esterified hydroxyalkyl sulfonyl amido or hydroxyalkyl amino sulfonyl group, a quaternised or non-quaternised amino alkyl sulfonyl amido group, or a substituted alkyl amino sulfonyl group, or a halogen alkyl sulfonyl amido or halogen alkyl amino sulfonyl group or a vinyl sulfonylamido or a substituted vinyl sulfonamido group, the reactive group being an epoxy or halohydrin group, the reactive group being an ethylenimino or N-acylated ethylenimino group or a —CO—NH—CH$_2$—CH$_2$—X group, wherein X is a halogen atom, a quaternary ammonium group or O-acyl and acyl is derived from an organic or inorganic acid, or a beta-substituted ethylamine group, the reactive group being a N-methylol group or an O-derivative thereof; or with other reactive groups; in each case from one of the following classes: anthracene dyes, azo dyes, e.g. monoazo dyes, disazo or polyazo dyes, nitro dyes, porphines; or azaporphines;

for example, a radical selected from the group comprising or preferably consisting of an acridine dye, an anthraquinone dye, an azamethine dye; an azo dye, e.g. monoazo, disazo or polyazo dye; a benzodifuranone dye, a coumarin dye, a diketopyrrolopyrrol dye, an oxazine dye, e.g. phenoxazine; a dioxazine dye, a carbonyl dye, e.g. indigoid or alizarine; a methine dye, e.g. a phenylogous methin dye, such as diaryl(e.g. phenyl)-methane or triarylmethane, e.g. phenolphthalein or malachite green, or a polymethine, e.g. pinacyanol or pelargonidine; a polymethine dye, a naphthalimide dye, a naphthoquinone dye, a nitroaryl dye, an oxazine dye, e.g. phenoxazine; a perinone dye, a perylene dye, a phenazine dye, a polyaza-annulene dye, e.g. phthalocyanine; a pyrenequinone dye, a quinacridone dye, a quinoneimine dye, a quinophtalone dye, a thiazine dye, e.g. phenothiazine; a thioxanthene dye, an aryl-carbonium dye and a xanthene dye and more preferably the radical of an anthraquinone, monoazo, disazo, polyazo, phthalocyanine and a dioxazine dye, where each of the dye radicals mentioned hereinbefore may be unsubstituted or substituted by one or more, e.g. one to four, substitutents, with the substitutents especially selected from the group consisting of $C_1$-$C_{10}$-alkyl, hydroxyl, sulfo (—$SO_2OH$) and/or sulfato (—$OSO_2$—OH)-substituted $C_1$-$C_{10}$-alkyl, $C_1$-$C_{10}$-alkoxy, hydroxyl, sulfo and/or sulfato substituted $C_1$-$C_{10}$-alkoxy, trifluoromethyl, hydroxyl, halogen, especially fluoro, chloro, bromo or iodo, carboxyl (—COOH), sulfo, sulfato, phosphono (—P(=O)(OH)$_2$), phospho (—O—P(=O)(OH)$_2$), cyano, nitro, amidino, ureido, carbamoyl, sulfamoyl, amino, $C_1$-$C_{10}$-alkanoylamino, such as acetylamino, mono- or di-($C_1$-$C_{12}$-alkyl)amino, a cationic quaternary ammonium (e.g. of the formula N(G)$_3^+$ wherein G can have the same or different meanings and is $C_1$-$C_{12}$alkyl which can be interrupted by —O— and can be unsubstituted or substituted by hydroxyl or phenyl and wherein the phenyl radical can be further substituted by $C_1$-$C_8$-alkyl, $C_1$-$C_8$-alkoxy or halogen, or is phenyl that is unsubstituted or substituted by $C_1$-$C_8$-alkyl, $C_1$-$C_8$-alkoxy or halogen; most preferably G is $C_1$-$C_{12}$alkyl) or a cationic phosphonium (especially of the formula —P(G)$_3^+$ wherein G is as just defined) group and phenyl or benzoyl wherein phenyl or benzyol is unsubstituted or substituted in the phenyl ring by at least one of the substituents just mentioned above (preferably except for substituted phenyl or benzoyl), especially by $C_1$-$C_8$-alkyl, $C_1$-$C_8$-alkoxy, halogen or sulfo; where acidic (e.g. carboxyl, sulfo, sulfato, phosphono, phospho) or basic (e.g. amino, mono- or di-($C_1$-$C_{10}$-alkyl)amino) groups can also be present in anionic or cationic form, respectively (that is, forming salts).

In one embodiment, a chromophoric moiety is an unsubstituted or substituted anthraquinone moiety, especially selected from the group of radicals having the following formulae, wherein the "#" sign marks the end of the bond that binds to X in formula I (and in formula III):

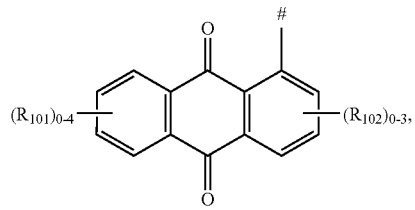

(1a)

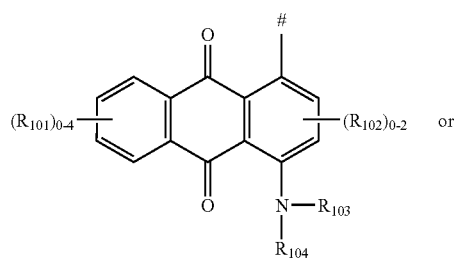

(1b)

or

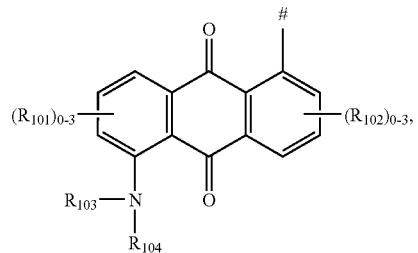

(1c)

wherein $R_{101}$ and $R_{102}$ (which may be absent (marked by the zero) or be present up to the given number of times with the index at the lower right) (instead of a hydrogen in the ring to which they are bound) are absent or are substitutents independently of each other selected from $C_1$-$C_{12}$alkyl, hydroxyl-substituted $C_1$-$C_{12}$-alkyl, $C_1$-$C_{12}$alkoxy, hydroxyl-substituted $C_1$-$C_{12}$alkoxy, trifluoromethyl, hydroxyl, halogen, especially fluoro, chloro, bromo or iodo, carboxyl (—COOH), sulfo (S(O)$_2$OH), sulfato (—O—S(O)$_2$OH), phosphono (—P(=O)(OH)$_2$), phospho (—O—P(=O)(OH)$_2$), cyano, nitro, amidino, ureido, carbamoyl, sulfamoyl, amino, $C_1$-$C_{10}$-alkanoylamino, such as acetylamino, mono- or di-($C_1$-$C_{12}$-alkyl)amino, a cationic quaternary ammonium (e.g. of the formula —N(G)$_3^+$ wherein G can have the same or different meanings and is $C_1$-$C_{12}$alkyl which can be interrupted by —O— and can be unsubstituted or substituted by hydroxyl or phenyl and wherein the phenyl radical can be further substituted by $C_1$-$C_8$-alkyl, $C_1$-$C_8$-alkoxy or halogen, or is phenyl that is unsubstituted or substituted by $C_1$-$C_8$-alkyl, $C_1$-$C_8$-alkoxy or halogen; most preferably G is $C_1$-$C_{12}$alkyl) or a cationic phosphonium (especially of the formula —P(G)$_3^+$ wherein G is as just defined) group or phenyl or benzoyl wherein phenyl or benzyol is unsubstituted or substituted in the phenyl ring by at least one of the substituents just mentioned above (preferably except for substituted phenyl or benzoyl), especially by $C_1$-$C_8$-alkyl, $C_1$-$C_8$-alkoxy, halogen or sulfo; where acidic (e.g. carboxyl, sulfo, sulfato, phosphono, phospho) or basic (e.g. amino, mono- or di-($C_1$-$C_{10}$-alkyl)amino) groups can also be present in anionic or cationic form, respectively (that is, forming salts); and $R_{103}$ and $R_{104}$ are independently selected from the group consisting of hydrogen, $C_1$-$C_{12}$-alkyl, hydroxyl-substituted $C_1$-$C_{12}$alkyl, or phenyl or phenyl-$C_1$-$C_{10}$alkyl, in both of which phenyl is unsubstituted or substituted by one or more, especially up to three, moieties independently selected from $C_1$-$C_{12}$alkyl, hydroxyl-substituted $C_1$-$C_{12}$-alkyl, $C_1$-$C_{12}$alkoxy, hydroxyl-substituted $C_1$-$C_{12}$alkoxy, trifluoromethyl, hydroxyl, halogen, especially fluoro, chloro, bromo or iodo, carboxyl, sulfo, sulfato, phosphono, phospho (—O—P(=O)(OH)$_2$), cyano, nitro, amidino, ureido, carbamoyl, sulfamoyl, amino, $C_1$-$C_{10}$-alkanoylamino, such as acetylamino, mono- or di-($C_1$-$C_{12}$-alkyl)amino, phenyl or benzoyl wherein phenyl or benzyol is unsubstituted or substituted in the phenyl ring by at least one of the substituents just mentioned (preferably except for substituted phenyl or benzoyl), especially by $C_1$-$C_8$-alkyl, $C_1$-$C_8$-alkoxy, halogen or sulfo; where acidic (e.g. carboxyl, sulfo, sulfato, phosphono, phospho) or basic (e.g. amino, mono- or di-($C_1$-$C_{10}$-alkyl)amino) groups can also be present in anionic or cationic form, respectively (that is, forming salts); where phenyl or phenyl-$C_1$-$C_{10}$alkyl are preferably substituted by $C_1$-$C_8$alkyl, $C_1$-$C_8$alkoxy, halogen, sulfo, hydroxy or amino; and where it is preferred that at least one of $R_{103}$ and $R_{104}$ is hydrogen.

The index at the lower right of the moieties $R_{101}$, $R_{102}$, $R_{103}$ and $R_{104}$ of the formulae 1a, 1b and 1c mean that zero to two ("0-2"), zero to three ("0-3") or zero to four ("0-4") of said moieties can be present.

In substituted $C_1$-$C_{12}$-alkyl, one or more, especially up to three, substituents are present which, independently of each other, are preferably selected from the group consisting of trifluoromethyl, hydroxyl, halogen, especially fluoro, chloro, bromo or iodo, carboxyl (—COOH), sulfo (S(O)$_2$OH), sulfato (—O—S(O)$_2$OH), phosphono (—P(=O)(OH)$_2$), phospho (—O—P(=O)(OH)$_2$), cyano, nitro, amidino, ureido, carbamoyl, sulfamoyl, amino, $C_1$-$C_{10}$-alkanoylamino, such as acetylamino, mono- or di-($C_1$-$C_{12}$-alkyl)amino, or phenyl or benzoyl wherein phenyl or benzoyl is unsubstituted or substituted in the phenyl ring by at least one of the substituents just mentioned (preferably except for substituted phenyl or benzoyl), especially by $C_1$-$C_8$-alkyl, $C_1$-$C_8$-alkoxy, halogen or sulfo; where acidic (e.g. carboxyl, sulfo, sulfato, phosphono, phospho) or basic (e.g. amino, mono- or di-($C_1$-$C_{10}$-alkyl)amino) groups can also be present in anionic or cationic form, respectively (that is, forming salts).

In substituted $C_1$-$C_{25}$-alkylene, which alkylene may be bound and/or be interrupted by at least one of the radicals selected from the group consisting of —O—, —S—, —N($R_4$)—, —CO—, —O—CO—, —CO—O—, —N($R_4$)—CO—, —CO—N($R_4$)— and phenylene, wherein $R_4$ is hydrogen or unsubstituted or substituted $C_1$-$C_{12}$alkyl, one or more, especially up to three, substituents are present, which, independently of each other, are selected from those just mentioned for $C_1$-$C_{25}$-alkyl the substituents and from unsubstituted or substituted $C_1$-$C_{12}$alkyl $R_4$.

In hydroxyl-substituted (e.g. $C_1$-$C_{12}$) alkyl, one or more hydroxyl groups can be present, preferably one or two.

In preferred polysiloxanes of the invention, the organic dye moietes (Dye) are selected from cationic dye moieties, whose positive charges are compensated by suitable anions.

Examples for classes of cationic dye moieties include those of anthraquinone, acridine, azo, azamethine, hydrazomethine, triphenylmethane, benzodifuranone, coumarine, diketopyrrolopyrrol, dioxazine, diphenylmethane, formazane, indigoid indophenol, naphthalimide, naphthoquinone, nitroaryl, merocyanine, methine oxazine, perinone, perylene, pyrenequinone, phtalocyanine, phenazine, quinoneimine, quinacridone, quinophtalone, styryl, stilbene, xanthene, thiazine and thioxanthene dyes; more preferably, the organic dye moietes are selected from cationic azo, azomethine, hydrazomethine, merocyanine, methine, triphenylmethane and styryl dye radicals.

"Anion" generally denotes any colorless anion, for example, an organic or inorganic anion, such as halide, preferably chloride and fluoride, sulfate, hydrogen sulfate, phosphate, boron tetrafluoride, carbonate, bicarbonate, oxalate or $C_1$-$C_8$alkyl sulfate such as methyl sulfate or ethyl sulfate; anion also denotes lactate, formate, acetate, propionate or a complex anion (e.g. from Zn or Al), such as the zinc chloride double salt. In a preferred class of polysiloxane dyes according to the invention, the organic dye moieties Dye thus are selected from cationic moieties, whose positive charges are compensated by suitable anions selected from halide, sulfate, hydrogen sulfate, phosphate, boron tetrafluoride, carbonate, bicarbonate, oxalate, $C_1$-$C_8$alkyl sulfate, lactate, formate, acetate, propionate or a zinc or aluminum complex anion.

The organic dye moiety Dye may also be derived from dyes as listed below (section: use of the present dyes for hair coloration) for concomitant use along with the dye of the invention.

Most preferably, all radicals Dye in the present polymeric particle are of the same type.

Some preferred radicals Dye are of the formulae

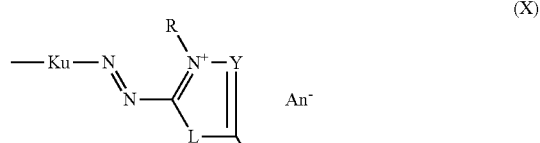
(X)

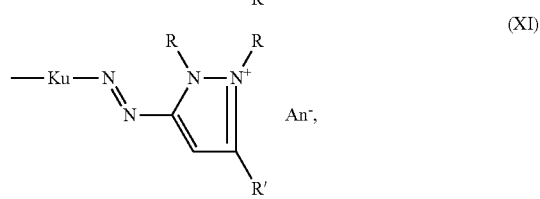
(XI)

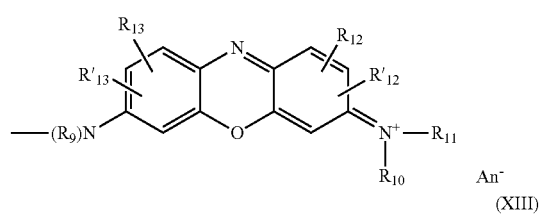
(XII)

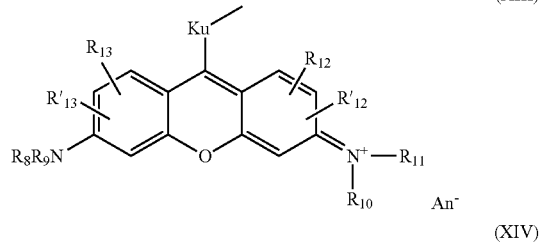
(XIII)

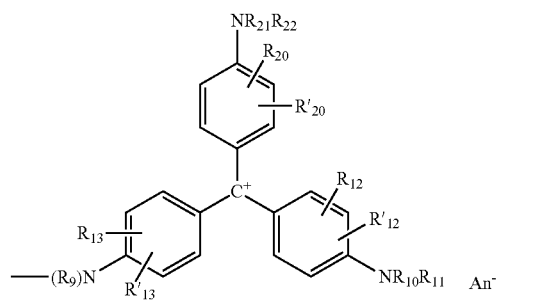
(XIV)

where

An$^-$ stands for an equivalent of a colorless anion;

Ku is a divalent radical of a coupling component of the aniline or phenol series or the radical of a heterocyclic coupling component, L is O, S or NR$^1$;

Y is CR$^3$ or N;

R is $C_1$-$C_4$alkyl;

R' is hydrogen, $C_1$-$C_4$alkyl, Cl, nitro, amino, $C_1$-$C_4$monoalkylamino or di-$C_1$-$C_4$alkylamino;

R$^1$ is H or $C_1$-$C_4$alkyl;

$R^3$ is H, $C_1$-$C_4$alkyl, or $C_1$-$C_4$alkyl substituted by OH—, $C_1$-$C_4$alkoxy-, halogen-, CN—, amino-, $C_1$-$C_4$monoalkylamino- or di-$C_1$-$C_4$alkylamino;

$R_8$, $R_9$, $R_{10}$, $R_{11}$, $R_{21}$ and $R_{22}$ are each independently of the others hydrogen or $C_1$-$C_4$alkyl;

$R_{12}$, $R'_{12}$, $R_{13}$, $R'_{13}$, $R_{20}$ and $R'_{20}$ are each independently of the other hydrogen, $C_1$-$C_4$alkyl or $C_1$-$C_4$alkoxy;

or one or more pairs of residues $R_8$, $R_9$, $R_{13}$, $R'_{13}$; and/or $R_{10}$, $R_{11}$, $R_{12}$, $R'_{12}$; and/or $R_{20}$, $R'_{20}$, $R_{21}$, $R_{22}$, bonding directly to the same phenyl ring or connected via nitrogen to said ring, together with the atoms they are attached to and further intermediary atoms, if present, form an aliphatic or aromatic, preferably 5- or 6-membered, ring.

In the dyes of the above formulae, Ku is in particular the radical of a coupling component of the formula

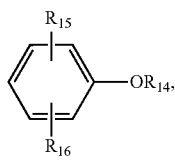
(7)

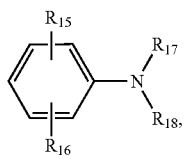
(8)

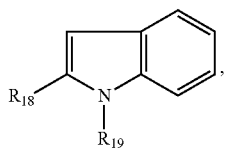
(9)

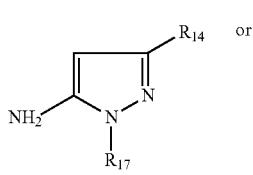
or
(10)

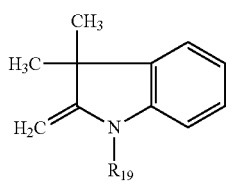
(11)

where $R_{14}$ is hydrogen or unsubstituted or OH—, $C_1$-$C_4$alkoxy-, halogen-, CN—, amino-, $C_1$-$C_4$monoalkylamino- or di-$C_1$-$C_4$alkylamino-substituted $C_1$-$C_4$alkyl, $R_{15}$ and $R_{16}$ are each independently of the other hydrogen, $C_1$-$C_4$alkyl, $C_1$-$C_4$alkoxy or halogen, $R_{17}$ and $R_{18}$ are each independently of the other hydrogen, unsubstituted or OH—, $O_1$—$C_4$alkoxy-, halogen-, CN—, amino-, $C_1$-$C_4$monoalkylamino- or di-$C_1$-$C_4$alkylamino-substituted $C_1$-$C_4$alkyl, or $R_{17}$ and $R_{18}$ are together with the nitrogen atom joining them together a 5- or 6-membered ring, or $R_{15}$ and $R_{17}$ are together with the nitrogen and carbon atoms joining them together a 5- or 6-membered ring, or $R_{16}$ and $R_{18}$ are together with the nitrogen and carbon atoms joining them together a 5- or 6-membered ring, and $R_{19}$ is hydrogen or unsubstituted or OH—, $C_1$-$C_4$alkoxy-, halogen-, CN—, amino-, $C_1$-$C_4$monoalkylamino- or di-$C_1$-$C_4$alkylamino-substituted $C_1$-$C_4$alkyl, while the open bonds of this divalent residue are formed by abstraction of 2 hydrogen atoms, preferably on 2 different atoms of the above structure.

If one or more pairs of residues $R_8$, $R_9$, $R_{13}$, $R'_{13}$; and/or $R_{10}$, $R_{11}$, $R_{12}$, $R'_{12}$; and/or $R_{20}$, $R'_{20}$, $R_{21}$, $R_{22}$; and/or $R_{17}$ and $R_{18}$ are to combine with the nitrogen atom joining them together into a 5- or 6-membered ring, this ring is in particular a pyrrolidine, piperidine, morpholine or piperazine ring. These rings can be further substituted, for example by $C_1$-$C_4$alkyl or $C_1$-$C_4$alkoxy. Preference, however, is given to the unsubstituted rings.

If $R_{12}$ and $R'_{12}$ or $R_{13}$ and $R'_{13}$ or $R_{20}$ and $R'_{20}$ or $R_{15}$ and $R_{17}$ or $R_{16}$ and $R_{18}$ are combined with the atoms joining them together into a 5- or 6-membered ring, this ring may contain a further heteroatom, for example oxygen or sulfur. Moreover, the ring may be substituted, for example by hydroxyl, alkoxy, alkyl, halogen or CN, or carry a further fused-on benzene ring. Preferred rings formed by $R_{15}$ and $R_{17}$ or $R_{16}$ and $R_{18}$ and the carbon atoms joining them together and the nitrogen atom are pyrroline, dihydrooxazine and di- or tetrahydropyridine rings carrying 0 to 4 methyl groups. Preferred rings formed by $R_{12}$ and $R'_{12}$ or $R_{13}$ and $R'_{13}$ or $R_{20}$ and $R'_{20}$ and the carbon atoms joining them together are phenyl or tetrahydrophenyl rings.

In particular Ku is the radical of a coupling component of the formula

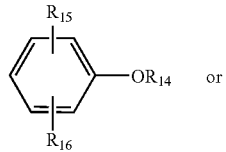
or
(7)

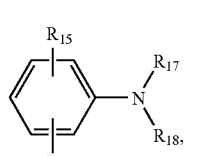
(8)

where $R_{14}$ is hydrogen or unsubstituted $C_1$-$C_4$alkyl, $R_{15}$ and $R_{16}$ are each independently of the other hydrogen, $C_1$-$C_4$alkyl, $C_1$-$C_4$alkoxy or halogen, $R_{17}$ and $R_{18}$ are each independently of the other hydrogen or unsubstituted $C_1$-$C_4$alkyl, or $R_{17}$ and $R_{18}$ are together with the nitrogen atom joining them together a pyrrolidine, piperidine, morpholine or piperazine ring, or $R_{15}$ and $R_{17}$ are together with the nitrogen and carbon atom joining them together a pyrrolidine, piperidine, morpholine or piperazine ring, or $R_{16}$ and $R_{18}$ are together with the nitrogen and carbon atom joining them together a pyrrolidine, piperidine, morpholine or piperazine ring, and $R_{19}$ is hydrogen or unsubstituted $C_1$-$C_4$alkyl.

Especially preferred dyes contain moieties T-Dye linked to Si which stand for a radical of the formula

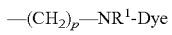
—(CH$_2$)$_p$—NR$^1$-Dye wherein
p is 2, 3 or 4;
Dye is selected from radicals of a cationic azo, azomethine, hydrazomethine, merocyanine, methine, triphenylmethane and styryl dyes such as the radical of the formula

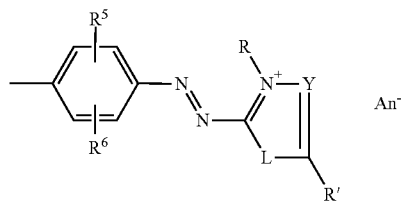

where
An$^-$ stands for an equivalent of a colorless anion;
L is O, S or NR$^1$;
Y is CR$^3$ or N;
R is C$_1$-C$_4$alkyl;
R' is hydrogen, C$_1$-C$_4$alkyl, Cl, nitro, amino, C$_1$-C$_4$monoalkylamino or di-C$_1$-C$_4$alkylamino;
R$^3$ is H, C$_1$-C$_4$alkyl, or C$_1$-C$_4$alkyl substituted by OH—, C$_1$-C$_4$alkoxy-, halogen-, CN—, amino-, C$_1$-C$_4$monoalkylamino- or di-C$_1$-C$_4$alkylamino;
R$^5$ and R$^6$ are each independently of the other hydrogen, C$_1$-C$_4$alkyl, C$_1$-C$_4$alkoxy or halogen;
and
R$^1$ is H or C$_1$-C$_4$alkyl.

Wherever mentioned, asymmetric spacer groups such as COO or CON(R$^1$) may be inserted in each way; for example, the ester group COO includes the inverse ester group OCO, or the amide group CON(R$^1$) includes the inverse amide N(R$^1$)CO.

Any carbocyclic or heterocyclic, non-aromatic or preferably aromatic ring of 5 to 7 ring atoms in total formed by two neighbouring residues as an organic bridging group together with their anchor atoms often is selected from aryl, heteroaryl, cycloalkyl, or cycloaliphatic unsaturated moieties as explained below.

Halogen denotes I, Br, Cl, F, preferably Cl, F, especially Cl.

Alkyl stands for any acyclic saturated monovalent hydrocarbyl group; alkenyl denotes such a group but containing at least one carbon-carbon double bond (such as in allyl); similarly, alkynyl denotes such a group but containing at least one carbon-carbon triple bond (such as in propargyl). In case that an alkenyl or alkynyl group contains more than one double bond, these bonds usually are not cumulated, but may be arranged in an alternating order, such as in —[CH=CH—]$_n$ or —[CH=C(CH$_3$)—]$_n$, where n may be, for example, from the range 2-50. Where not defined otherwise, preferred alkyl contains 1-22 carbon atoms; preferred alkenyl and alkinyl each contains 2-22 carbon atoms, especially 3-22 carbon atoms.

Where indicated as interrupted, any alkyl moiety of more than one, especially more than 2 carbon atoms, or such alkyl or alkylene moieties which are part of another moiety, may be interrupted by a heterofunction such as O, S, COO, OCNR10, OCOO, OCONR10, NR10CNR10, or NR10, where R10 is H, C$_1$-C$_{12}$alkyl, C$_3$-C$_{12}$cycloalkyl, phenyl. They can be interrupted by one or more of these spacer groups, one group in each case being inserted, in general, into one carbon-carbon bond, with hetero-hetero bonds, for example O—O, S—S, NH—NH, etc., not occurring; if the interrupted alkyl is additionally substituted, the substituents are generally not α to the heteroatom. If two or more interrupting groups of the type —O—, —NR10-, —S— occur in one radical, they often are identical.

The term alkyl, wherever used, thus mainly embraces especially uninterrupted and, where appropriate, substituted C$_1$-C$_{22}$alkyl such as methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl. Alkoxy is alkyl-O—; alkylthio is alkyl-S—.

The term alkenyl, wherever used, thus mainly embraces especially uninterrupted and, where appropriate, substituted C$_2$-C$_{22}$alkyl such as vinyl, allyl, etc.

Aliphatic cyclic moieties include cycloalkyl, aliphatic heterocyclic moieties, as well as unsaturated variants thereof such as cycloalkenyl. Cycloalkyl such as C$_3$-C$_{18}$cycloalkyl, is preferably C$_3$-C$_{12}$cycloalkyl or said cycloalkyl substituted by one to three C$_1$-C$_4$alkyl groups, and includes cyclopropyl, cyclobutyl, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl, cyclooctyl, cyclononyl, cyclodecyl, cyclododecyl, 1-adamantyl, or 2-adamantyl. Cyclohexyl, 1-adamantyl and cyclopentyl are most preferred. C$_3$-C$_{12}$cycloalkyl includes cyclopropyl, cyclobutyl, cyclopentyl, cyclohexyl, cycloheptyl, cyclooctyl, cyclononyl, cyclodecyl, cycloundecyl, cyclododecyl; preferred among these residues are C$_3$-C$_6$cycloalkyl as well as cyclododecyl, especially cyclohexyl. Further ring structures occurring are heterocyclic aliphatic rings usually containing 5 to 7 ring members, among them at least 1, especially 1-3, heteromoieties, usually selected from O, S, NR10, where R10 is as explained above for interrupting NR10-groups; examples include C$_4$-C$_{18}$cycloalkyl, which is interrupted by S, O, or NR10, such as piperidyl, tetrahydrofuranyl, piperazinyl and morpholinyl. Unsaturated variants may be derived from these structures by abstraction of a hydrogen atom on 2 adjacent ring members with formation of a double bond between them; an example for such a moiety is cyclohexenyl.

Alkoxy such as C$_1$-C$_{24}$alkoxy is a straight-chain or branched radical, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy.

C$_6$-C$_{18}$cycloalkoxy is, for example, cyclopentyloxy, cyclohexyloxy, cycloheptyloxy or cyclooctyloxy, or said cycloalkoxy substituted by one to three C$_1$-C$_4$alkyl, for example, methylcyclopentyloxy, dimethylcyclopentyloxy, methylcyclohexyloxy, dimethylcyclohexyloxy, trimethylcyclohexyloxy, or tert-butylcyclohexyloxy.

Coloured means that a compound of the formula I absorbs at least more or less selectively within the visible part of the spectrum (wavelengths about 400 to about 800 nm) at preferably one limited wavelength range. The colour realized with the eye then corresponds to the respective complementary colour of the absorbed spectral area(s) which results from the rest of the spectrum in the wavelength area between about 400 to about 800 nm.

General Use of the Dyes

The novel compounds can be used as colorants (as such or in the form of compositions with one or more additives). Substrates, which can be colored using a compound according to the invention, includes materials, goods, formulations, natural substrates within the living world, such as hair, skin, nails or teeth, or any other tangible things that can be colored by dying and/or pigmenting with the compounds of the formula I.

Materials that can be colored by the compounds of the formula I include for example plastics materials, wood, stone, sand, cement, mortars, resins, coating materials, metals, alloys, textile materials, paper, cardboard, leather, dentine, enamel, or other natural or artificial materials, each of which can be colored on the surface, by impregnation also regarding inner surfaces, or by bulk addition during production or processing where possible, e.g. in the case of plastics, cement, mortars, resins, paper or coating materials. Intermediate materials to obtain final materials or goods are also included. Inorganic materials like silica, alumina, alumo-silica or titano materials can be colored by partial hydrolytic break-up of the claimed clusters in order to incorporate the color-functionalized, now partially opened clusters covalently to said inorganic materials forming organic-inorganic nano-hybridmaterials. These materials are useful as optical indicators or detectors e.g. in sensing devices. The colored nano-clusters can be used to produce colored coatings on ceramics or in concrete materials.

Goods can be any finished articles or objects or product parts, such as e-paper, fabrics, cloths, shoes, furniture, vehicles or vehicle components, e.g. tires, print products, electronic products, packaging materials, machines, tools, instruments, music instruments, prosthesis, devices, containers, floor coverings, or the like, including also incomplete products, such as semi-finished products.

Formulations can be therapeutic, diagnostic, cosmetic, fertilizer, dental, cleaning or other homecare compositions which, in addition comprise other customary additives (e.g. solvents, stabilizers etc.) and where present active entities (e.g. pharmaceutically active entities). Other formulations include paints, lacquers, electrostatic toners, inks additives to plastics and polymers, sealants, colorfilters, colored adhesives and/or printing systems.

Natural substrates within the living world can, for example, be hair, nails, skin, teeth, feathers or the like.

In addition, the use of the compounds of the formula I may be for example in packaging, tagging and labeling applications, and the like.

The present polysiloxanes are useful as dyes or nanopigments for the coloration mainly of organic materials, such as keratin-containing fibers, wool, leather, silk, cellulose or polyamides, cotton or nylon, and preferably human hair. The dyeings obtained are distinguished by their depth of shade and their good fastness properties to washing, such as, for example, fastness to light, shampooing and rubbing. The invention thus includes a composition comprising at least polysiloxane dye as defined above and a further component selected from synthetic organic polymers, natural organic polymers, cosmetically acceptable carriers, further dyes, oxidative agents and detergents. Preferred compositions of the invention comprise in addition at least one single further direct dye and/or an oxidative agent. Compositions according to the invention often are cosmetic compositions, e.g. in form of a shampoo, a conditioner, a gel or an emulsion. The invention consequently includes a method which comprises treating the organic material with at least one dye as defined above, an oxidative agent and, optionally, a further direct dye.

The method according to the invention also includes treating the organic material with at least one dye of the invention and at least one single oxidative dye, or treating the organic material with a dye of the invention and at least one single oxidative dye and an oxidative agent.

If used for colouring synthetic materials, for example, the present dyes are often used in combination with customary additives such as antioxidants, radical scavengers and/or UV absorbers; examples for such components include those known in the art, see e.g. those disclosed in WO05/030856: UV absorber of component (c), page 1, line 32, until page 13, line 22; page 17, line 21, until page 23, line 25 for polymeric substrates; page 31, line 21, until page 56, line 7, for specific radical scavengers; page 56, line 21, until page 60, line 24, for antioxidants; page 60, line 26, until page 66, line 11, for further additives and dosages of additives; page 66, line 13, until page 68, line 29, of said document for the incorporation of dyes and additives and uses of the compositions.

In consequence, the invention further pertains to a method of dyeing an organic material, which comprises treating the organic material with at least one polysiloxane dye or a composition containing said dye as defined above, optionally in combination with an oxidative agent and/or a further direct dye, e.g. additionally with at least one single oxidative dye, or treating the organic material with a dye as defined in claim 1 and at least one single oxidative dye and an oxidative agent.

Use of the Present Dyes for Hair Coloration

The polysiloxane dye of the invention is advantageously used for the coloration of keratin-containing fibers such as human hair.

Generally, hair dyeing agents on a synthetic base may be classiefied into three groups:

temporary dyeing agents semipermanent dyeing agents, and permanent dyeing agents.

The multiplicity of shades of the dyes can be increased by combination with other dyes.

Therefore the dyes of the present invention may be combined with dyes of the same or other classes of dyes, especially with direct dyes, oxidation dyes; dye precursor combinations of a coupler compound as well as a diazotized compound, or a capped diazotized compound; and/or cationic reactive dyes.

Direct dyes are of natural origin or may be prepared synthetically. They are uncharged, cationic or anionic, such as acid dyes.

The dyes of the invention may be used in combination with at least one single direct dye different from the present dyes e.g. of formula I or II.

Direct dyes do not require any addition of an oxidizing agent to develop their dyeing effect. Accordingly the dyeing results are less permanent than those obtained with permanent dyeing compositions. Direct dyes are therefore preferably used for semipermanent hair dyeings.

Examples of direct dyes are described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, and in "Europäisches Inventar der Kosmetikrohstoffe", 1996, published by The European Commission, obtainable in diskette form from the Bundesverband der deutschen Industrie- und Handelsunternehmen für Arzneimittel, Reformwaren und Korperpflegemittel e.V., Mannheim.

More preferred direct dyes which are useful for the combination with at least one single dye of the present invention, especially for semi permanent dyeing, are:

2-amino-3-nitrophenol, 2-amino-4-hydroxyethylamino-anisole sulfate, 2-amino-6-chloro-4-nitrophenol, 2-chloro-5-nitro-N-hydroxyethylene-p-phenylendiamine, 2-hydroxyethyl-picramic acid, 2,6-diamino-3-((pyridine-3yl)-azo) pyridine, 2-nitro-5-glyceryl-methylanil., 3-methylamino-4-nitro-phenoxyethanol, 4-amino-2-nitrodiphenyleneamine-2'-carboxilic acid, 6-nitro-1,2,3, 4,-tetrahydroquinoxal., 4-N-ethyl-1,4-bis(2'-hydroxyethylamino-2-nitrobenzene hydrochloride, 1-methyl-3-nitro-4-(2'-hydroxyethyl)-aminobenzene, 3-nitro-p-hydroxyethylaminophenol, 4-amino-3-nitrophenol, 4-hydroxypropylamine-3-nitrophenol, hydroxyanthrylaminopropylmethyl morphlino methosulfate, 4-nitrophenyl-aminoethylurea, 6-nitro-p-toluidine, Acid Blue 62, Acid Blue 9, Acid Red 35, Acid Red 87 (Eosin), Acid Violet 43, Acid Yellow 1, Basic Blue 3, Basic Blue 6, Basic Blue 7, Basic Blue 9, Basic Blue 12, Basic Blue 26, Basic Blue 99, Basic Brown 16, Basic Brown 17, Basic Red 2, Basic Red 22, Basic Red 76, Basic Violet 14, Basic Yellow 57, Basic Yellow 9, Disperse Blue 3, Disperse Orange 3, Disperse Red 17, Disperse Violet 1, Disperse Violet 4, Disperse Black 9, Fast Green FCF, HC Blue 2, HC Blue 7, HC Blue 8, HC Blue 12, HC Orange 1, HC Orange 2, HC Red 1, HC Red 10-11, HC Red 13, HC Red 16, HC Red 3, HC Red BN, HC Red 7, HC Violet 1, HC Violet 2, HC Yellow 2, HC Yellow 5, HC Yellow 5, HC Yellow 6, HC Yellow 7, HC Yellow 9, HC Yellow 12, HC Red 8, hydroxyethyl-2-nitro-p-toluidine, N,N-Bis-(2-Hydroxyethyl)-2-nitro-p-phenylendiamine, HC Violet BS, Picramic Acid, Solvent Green 7.

Furthermore, the dyes of the present invention may be combined with at least one cationic azo dye, for example the compounds disclosed in GB-A-2 319 776 as well as the oxazine dyes described in DE-A-299 12 327 and mixtures thereof with the other direct dyes mentioned therein, and even more preferred with cationic dyes such as Basic Yellow 87, Basic Orange 31 or Basic Red 51, or with cationic dyes as described in WO 01/66646, especially example 4, or with cationic dyes as described in WO 02/31056, especially example 6, the compound of formula 106; or the cationic dye of formula (3) as described in EP-A-714,954, or with a yellow cationic dye of formula

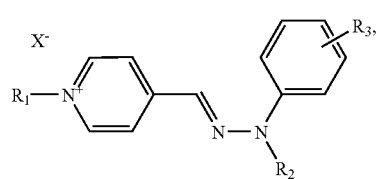

(DD1)

wherein $R_1$ and $R_2$ are each independently of the other a $C_1$-$C_8$alkyl; or an unsubstituted or substituted benzyl;

$R_3$ is hydrogen; $C_1$-$C_8$alkyl; $C_1$-$C_8$alkoxy; cyanide; or halide; preferably hydrogen; and $X^-$ is an anion; and preferably a compound of formula (DD1), wherein $R_1$ is methyl; $R_2$ is benzyl; $R_3$ is hydrogen; and $X^-$ is an anion; or wherein $R_1$ is benzyl; $R_2$ is benzyl; $R_3$ is hydrogen; and $X^-$ is an anion; or wherein $R_1$ is benzyl; $R_2$ is methyl; $R_3$ is hydrogen; and $X^-$ is an anion.

Furthermore, cationic nitroaniline and anthraquinone dyes are useful for a combination with a dye of the present invention for example the dyes as described in the following patent specifications: U.S. Pat. No. 5,298,029, especially in col 2, l. 33 to col 5, l. 38; U.S. Pat. No. 5,360,930, especially in col 2, l. 38 to col 5, l. 49; U.S. Pat. No. 5,169,403, especially in col 2, l. 30 to col 5, l. 38; U.S. Pat. No. 5,256,823, especially in col 4, l. 23 to col 5, l. 15; U.S. Pat. No. 5,135,543, especially in col 4, l. 24 to col 5, l. 16; EP-A-818 193, especially on p. 2, l. 40 to p. 3, l. 26; U.S. Pat. No. 5,486,629, especially in col 2, l. 34 to col 5, l. 29; and EP-A-758 547, especially on p. 7, l. 48 to p. 8, l. 19.

The dyes of the present invention may also be combined with acid dyes, for example the dyes which are known from the international names (Color index), or trade names.

Preferred acid dyes which are useful for the combination with a dye of the present invention are described in U.S. Pat. No. 6,248,314. They include Red Color No. 120, Yellow Color No. 4, Yellow Color No. 5, Red Color No. 201, Red Color No. 227, Orange Color No. 205, Brown Color No. 201, Red Color No. 502, Red Color No. 503, Red Color No. 504, Red Color No. 506, Orange Color No. 402, Yellow Color No. 402, Yellow Color No. 406, Yellow Color No. 407, Red Color No. 213, Red Color No. 214, Red Color No. 3, Red Color No. 104, Red Color No. 105(1), Red Color No. 106, Green Color No. 2, Green Color No. 3, Orange Color No. 207, Yellow Color No. 202(1), Yellow Color No. 202(2), Blue Color No. 202, Blue Color No. 203, Blue Color No. 205, Blue Color No. 2, Yellow Color No. 203, Blue Color No. 201, Green Color No. 201, Blue Color NO. 1, Red Color No. 230(1), Red Color No. 231, Red Color No. 232, Green Color No. 204, Green Color No. 205, Red Color No. 401, Yellow Color No. 403(1), Green Color No. 401, Green Color No. 402, Black Color No. 401 and Purple Color No. 401, especially Black Color No. 401, Purple Color 401, Orange Color No. 205.

These acid dyes may be used either as single component or in any combination thereof.

Hair dye compositions comprising an acid dye are known. They are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 253 and 254.

Hair dye compositions which comprise an acid dye have a pH of 2-6, preferably 2-5, more preferably 2.5-4.0.

The dyes according to the present invention may also readily be used in combination with acid dyes and/or adjuvants, for example acid dyes and an alkylene carbonate, as described in U.S. Pat. No. 6,248,314, especially in examples 1 and 2;

acid hair dye compositions comprising various kinds of organic solvents represented by benzyl alcohol as a penetrant solvent have good penetrability into hair, as described in Japanese Patent Application Laid-Open Nos. 210023/1986 and 101841/1995;

acid hair dye compositions with a water-soluble polymer or the like to prevent the drooping of the hair dye composition, as described for example in Japanese Patent Application Laid-Open Nos. 87450/1998, 255540/1997 and 245348/1996;

acid hair dye compositions with a water-soluble polymer of aromatic alcohols, lower alkylene carbonates, or the like as described in Japanese Patent Application Laid-Open No. 53970/1998 and Japanese Patent Invention No. 23911/1973.

The dyes according to the present invention may also be combined with uncharged dyes, for example selected from the group of the nitroanilines, nitrophenylenediamines, nitroaminophenols, anthraquinones, indophenols, phenazines, phenothiazines, bispyrazolons, bispyrazol aza derivatives and methines.

Furthermore, the dyes according to the present invention may also be used in combination with oxidation dye systems.

Oxidation dyes, which, in the initial state, are not dyes but dye precursors are classified according to their chemical properties into developer and coupler compounds.

Suitable oxidation dyes are described for example in
DE 19 959 479, especially in col 2, l. 6 to col 3, l. 11;
"Dermatology", edited by Ch. Culnan, H. Maibach, Verlag Marcel Dekker Inc., New York, Basle, 1986, Vol. 7, Ch. Zviak, The Science of Hair Care, chapter 8, on p. 264-267 (oxidation dyes);

Preferred developer compounds are for example primary aromatic amines, which are substituted in the para- or ortho-position with a substituted or unsubstituted hydroxy- or amino residue, or diaminopyridine derivatives, heterocyclic hydrazones, 4-aminopyrazol derivatives, 2,4,5,6-tetraminopyrimidine derivatives, or unsaturated aldehydes as described in DE 19 717 224, especially on p. 2, l. 50 to l. 66 and on p. 3 l. 8 to l. 12, or cationic developer compounds as described in WO 00/43367, especially on p., 2 l. 27 to p. 8, l. 24, in particular on p. 9, l. 22 to p. 11, l. 6.

Furthermore, developer compounds in their physiological compatible acid addition salt form, such as hydrochloride or sulfate can be used. Developer compounds, which have aromatic OH radicals are also suitable in their salt form together with a base, such as alkali metal-phenolates.

Preferred developer compounds are disclosed in DE 19959479, p. 2, l. 8-29.

More preferred developer compounds are p-phenylendiamine, p-toluoylendiamine, p-, m- o-aminophenol, N,N-bis-(2-hydroxyethyl)-p-phenylenediamine sulfate, 2-amino-4-hydroxyethylaminoanisole sulfate, hydroxyethyl-3,4-methylenedioxyanil., 1-(2'-hydroxyethyl)-2,5-diaminobenzene, 2,6-dimethoxy-3,5-diamino-pyridine, hydroxypropyl-bis-(N-hydroxyethyl-p-phenylenediamine) hydrochloride, hydroxyethyl-p-phenylenediamine sulfate, 4-amino-3-methylphenol, 4-methylaminophenol sulfate, 2-aminomethyl-4-aminophenol, 4,5-diamino-1-(2-hydroxyethyl)-1H-pyrazol, 4-amino-m-cresol, 6-amino-m-cresol, 5-amino-6-chloro-cresol, 2,4,5,6-tetraminopyrimidine, 2-hydroxy-4,5,6-triaminopyrimidine or 4-hydroxy-2,5,6-triaminopyrimidine sulfate.

Preferred coupler compounds are m-phenylendiamine derivatives, naphthole, resorcine and resorcine derivatives, pyrazolone and m-aminophenol derivatives, and most preferably the coupler compounds disclosed in DE 19959479, p. 1, l. 33 to p. 3, l. 11.

The dyes according to the present invention may also be used together with unsaturated aldehydes as disclosed in DE 19 717 224 (p. 2, l. 50 to l. 66 and on p. 3 l. 8 to l. 12) which may be used as direct dyes or, alternatively together with oxidation dye precursors.

Further preferred for a combination with a dye according to the present invention are the following oxidation dye precursors:
the developer/-coupler combination 2,4,5,6-tetraminopyrimidine and 2-methylresorcine for assessing of red shades;
p-toluenediamine and 4-amino-2-hydroxytoluene for assessing of blue-violet shades;
p-toluenediamine and 2-amino-4-hydroxyethylaminoanisole for assessing of blue shades;
p-toluenediamine and 2,4-diamino-phenoxyethynol for assessing of blue shades;
methyl-4-aminophenol and 4-amino-2-hydroxytoluene for assessing of orange shades;
p-toluenediamine and resorcine for assessing of brown-green shades;
p-toluenediamine and 1-naphthol for assessing of blue-violet shades, or
p-toluenediamine and 2-methylresorcine for assessing of brown-gold shades.

Furthermore, autooxidizable compounds may be used in combination with the dyes according to the present invention.

Autooxidizable compounds are aromatic compounds with more than two substituents in the aromatic ring, which have a very low redox potential and will therefore be oxidized when exposed to the air. The dyeings obtained with these compounds are very stable and resistant to shampoo.

Autooxidizable compounds are for example benzene, indol, or indol, especially 5,6-dihydroxyindol or 5,6-dihydroxyindol. derivatives as described in WO 99/20234, especially on p. 26, l. 10 to p. 28, l. 15, or in WO 00/28957 on p. 2, third paragraph.

Preferred autooxidizable benzene derivatives are 1,2,4-trihydroxybenzene, 1-methyl-2,4,5-trihydroxybenzene, 2,4-diamnio-6-methylphenol, 2-amino-4-methylaminophenol, 2,5-diamino-4-methyl-phenol, 2,6-diamino-4-diethylaminophenol, 2,6-diamino-1,4-dihydroxybenzene, and the salts of these compounds, which are accessible with acid.

Preferred autooxidizable indol derivatives are 5,6-dihydroxyindol, 2-methyl-5,6-dihydroxyindol, 3-methyl-5,6-dihydroxyindole, 1-methyl-5,6-dihydroxyindol, 2,3-dimethyl-5,6-dihydroxyindol, 5-methoxy-6-dihydroxyindol, 5-acetoxy-6-hydroixyindol, 5,6-diacetoxyindol, acid of 5,6-dihydroxyindol-2-carbonacid, and the salts of these compounds, which are accessible with acid.

The dyes according to the present invention may also be used in combination with naturally occurring dyes, such as henna red, henna neutral, henna black, camomile blossom, sandalwood, black tea, Rhamnus frangula bark, sage, campeche wood, madder root, catechu, sedre and alkanet root. Such dyeings are described, for example, in EP-A-404 868, especially on p. 3, l. 55 to p. 4, l. 9.

Furthermore, the dyes according to the present invention may also be used in combination with capped diazotised compounds.

Suitable diazotised compounds are for example the compounds of formulae (1)-(4) in WO 2004/019897 (bridging gages 1 and 2) and the corresponding watersoluble coupling components (I)-(IV) as disclosed in the same reference on p. 3 to 5.

Further preferred dyes or dye combinations which are useful for the combination with a dye according to the present invention are described in
(DC-01): WO 95/01772, wherein mixtures of at least two cationic dyes are disclosed, especially p. 2, l. 7 to p. 4, l. 1, preferably p. 4, l. 35 to p. 8, l. 21; formulations p. 11, last §-p. 28, l. 19;
(DC-02): U.S. Pat. No. 6,843,256, wherein cationic dyes are disclosed, especially the compounds of formulae (1), (2), (3) and (4) (col. 1, l. 27 col. 3, l. 20, and preferably the compounds as prepared in the examples 1 to 4 (col. 10, l. 42 to col. 13, l. 37; formulations col. 13, l. 38 to col. 15, l. 8;
(DC-03): EP 970 685, wherein direct dyes are described, especially p. 2, l. 44 to p. 9, l. 56 and preferably p. 9, l. 58 to p. 48, l. 12; processes for dyeing of keratin-containing fibers especially p. 50, l. 15 to 43; formulations p. 50, l. 46 to p. 51, l. 40;

(DC-04): DE-A-19 713 698, wherein direct dyes are described, especially p. 2, l. 61 to p. 3, l. 43; formulations p. 5, l. 26 to 60;

(DC-05): U.S. Pat. No. 6,368,360, wherein directed dyes (col. 4, l. 1 to col. 6, l. 31) and oxidizing agents (col. 6, l. 37-39) are disclosed; formulations col. 7, l. 47 to col. 9, l. 4;

(DC-06): EP 1 166 752, wherein cationic dyes (p. 3, l. 22 p. 4, l. 15) and anionic UV-absorbers (p. 4, l. 27-30) are disclosed; formulations p. 7, l. 50 p. 9, l. 56;

(DC-07): EP 998,908, wherein oxidation dyeings comprising a cationic direct dye and pyrazolo-[1,5-a]-pyrimidines (p. 2, l. 48 p. 4, l. 1) are disclosed; dyeing formulations p. 47, l. 25 to p. 50, l. 29;

(DC-08): FR-2788432, wherein combinations of cationic dyes with Arianors are disclosed, especially p. 53, l. 1 to p. 63, l. 23, more especially p. 51 to 52, most especially Basic Brown 17, Basic brown 16, Basic Red 76 and Basic Red 118, and/or at least one Basic Yellow 57, and/or at least one Basic Blue 99; or combinations of arianoren and/or oxidative dyes, especially p. 2, l. 16 to p. 3, l. 16; dyeing formulations on p. 53, l. 1 to p. 63, l. 23;

(DC-09): DE-A-19 713 698, wherein the combinations of direct dyes and permanent-wave fixing comprising an oxidation agent, an oxidation dye and a direct dye are disclosed; especially p. 4, l. 65 to p. 5, l. 59;

(DC-10): EP 850 638, wherein developer compounds and oxidizing agents are disclosed; especially p. 2, l. 27 to p. 7, l. 46 and preferably p. 7, l. 20 to p. 9, l. 26; dyeing formulations p. 2, l. 3-12 and l. 30 to p. 14, and p. 28, l. 35-p. 30, l. 20; preferably p. 30, l. 25-p. 32, l. 30;

(DC-11): U.S. Pat. No. 6,190,421 wherein extemporaneous mixtures of a composition (A) containing one or more oxidation dye precursors and optionally one or more couplers, of a composition (B), in powder form, containing one or more direct dyes (col. 5, l. 40 col. 7, l. 14), optionally dispersed in an organic pulverulent excipient and/or a mineral pulverulent excipient, and a composition (C) containing one or more oxidizing agents are disclosed; formulations col. 8, l. 60-col. 9, l. 56;

(DC-12): U.S. Pat. No. 6,228,129, wherein a ready-to-use composition comprising at least one oxidation base, at least one cationic direct dye and at least one enzyme of the 2-electron oxidoreductase type in the presence of at least one donor for the said enzyme are disclosed; especially col. 8, l. 17-col. 13, l. 65; dyeing formulations in col. 2, l. 16 to col. 25, l. 55, a multi-compartment dyeing device is described in col. 26, l. 13-24;

(DC-13): WO 99/20235, wherein compositions of at least one cationic dye and at least one nitrated benzene dye with cationic direct dyes and nitro benzene direct dyes are described; on p. 2, l. 1 to p. 7, l. 9, and p. 39, l. 1 to p. 40 l. 11, preferably p. 8, l. 12 to p. 25 l. 6, p. 26, l. 7 to p. 30, l. 15; p. 1, l. 25 to p. 8, l. 5, p. 30, l. 17 to p. 34 l. 25, p. 8, l. 12 to p. 25 l. 6, p. 35, l. 21 to 27, especially on p. 36, l. 1 to p. 37;

(DC-14): WO 99/20234, wherein compositions comprising at least one direct cationic dye and at least one autooxidisable dye, especially benzene, indol and indol. derivatives are described, preferably direct dyes on p. 2, l. 19 to p. 26, l. 4, and autooxidisable dyes as disclosed especially on p. 26, l. 10 to p. 28, l. 15; dyeing formulations especially on p. 34, l. 5 to p. 35, li 18;

(DC-15): EP 850 636, wherein oxidation dyeing compositions comprising at least one direct dye and at least one meta-aminophenol derivative as coupler component and at least one developer compound and an oxidizing agent are disclosed, especially p. 5, l. 41 to p. 7, l. 52, dyeing formulations p. 19, l. 50-p. 22, l. 12;

(DC-16): EP-A-850 637, wherein oxidation dyeing compositions comprising at least one oxidation base selected from para-phenylenediamines and bis(phenyl)alkylenediamines, and the acid-addition salts thereof, at least one coupler selected from meta-diphenols, and the acid-addition salts thereof, at least one cationic direct dye, and at least one oxidizing agent are disclosed, especially p. 6, l. 50 to p. 8, l. 44 are disclosed; dyeing formulations p. 21, l. 30-p. 22, l. 57;

(DC-17): WO 99/48856, wherein oxidation dyeing compositions comprising cationic couplers are disclosed, especially p. 9, l. 16-p. 13, l. 8, and p. 11, l. 20-p. 12, l. 13; dyeing formulations p. 36, l. 7-p. 39, l. 24;

(DC-18): DE 197 172 24, wherein dyeing agents comprising unsaturated aldehydes and coupler compounds and primary and secondary amino group compounds, nitrogen-containing heterocyclic compounds, amino acids, oligopeptids, aromatic hydroxy compounds, and/or at least one CH-active compound are disclosed p. 3, l. 42-p. 5 l. 25; dyeing formulations p. 8, l. 25 p. 9, l. 61.

In the dye combinations disclosed in the references (DC-01-DC-18) above, the dyes according to the present invention may be added to the dye combinations or dyeing formulations or one or more of the dye components may be replaced with at least one dye of the present invention.

The present invention also relates to formulations, which are used for the dyeing of organic materials, preferably keratin-containing fibers, and most preferably human hair, comprising at least one dye of the invention.

Preferably the dyes of the present invention are incorporated into the composition for treating organic material, preferably for dyeing in amounts of 0.001-5% by weight (hereinafter indicated merely by "%"), particularly 0.005-4%, more particularly 0.2-3%, based on the total weight of the composition.

The formulations may be applied on the keratin-containing fiber, preferably the human hair in different technical forms.

Technical forms of formulations are for example a solution, especially a thickened aqueous or aqueous alcoholic solution, a cream, foam, shampoo, powder, gel, or emulsion.

Customary the dyeing compositions are applied to the keratin-containing fiber in an amount of 50 to 100 g.

Preferred forms of formulations are ready-to-use compositions or multi-compartment dyeing devices or 'kits' or any of the multi-compartment packaging systems with compartments as described for example in U.S. Pat. No. 6,190,421, col 2, l. 16 to 31.

The pH value of the ready-to-use dyeing compositions is usually from 2 to 11, preferably from 5 to 10.

The dyeing compositions of the present invention are applied on the hair in a temperature range of 25 to 200, preferably 18 to 80, and most preferably from 20 to 40° C.

One preferred embodiment of the present invention relates to the formulation of dyes, wherein the dyes of the present invention are in powder form.

Powder formulations are preferably used if stability and/or solubility problems as for example described in DE 197 13 698, p. 2, l. 26 to 54 and p. 3, l. 51 to p. 4, l. 25, and p. 4, l. 41 to p. 5 l. 59.

Suitable cosmetic hair-care formulations are hair-treatment preparations, e.g. hair-washing preparations in the form of shampoos and conditioners, hair-care preparations, e.g. pre-treatment preparations or leave-on products such as sprays, creams, gels, lotions, mousses and oils, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or camomile.

For use on human hair, the dyeing compositions of the present invention can usually be incorporated into an aqueous cosmetic carrier. Suitable aqueous cosmetic carriers include, for example W/O, O/W, O/W/O, W/O/W or PIT emulsions and all kinds of microemulsions, creams, sprays, emulsions, gels, powders and also surfactant-containing foaming solutions, e.g. shampoos or other preparations, that are suitable for use on keratin-containing fibers. Such forms of use are described in detail in Research Disclosure 42448 (August 1999). If necessary, it is also possible to incorporate the dyeing compositions into anhydrous carriers, as described, for example, in U.S. Pat. No. 3,369,970, especially col 1, l. 70 to col 3, l. 55. The dyeing compositions according to the invention are also excellently suitable for the dyeing method described in DE-A-3 829 870 using a dyeing comb or a dyeing brush.

The constituents of the aqueous carrier are present in the dyeing compositions of the present invention in the customary amounts; for example emulsifiers may be present in the dyeing compositions in concentrations from 0.5 to 30% by weight and thickeners in concentrations from 0.1 to 25% by weight of the total dyeing composition.

Further carriers for dyeing compositions are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 243, l. 1 to p. 244, l. 12.

If the dyes of the present invention are used together with oxidation dyes and/or the addition salts thereof with an acid, they may be stored separately or together. Preferably the oxidation dyes and the direct dyes which are not stable to reduction are stored separately.

The dyes of the present invention may be stored in a liquid to paste-like preparation (aqueous or non-aqueous) or in the form of a dry powder.

When the dyes are stored separately, the reactive components are intimately mixed with one another directly before use. In the case of dry storage, a defined amount of hot (from 50 to 80° C.) water is usually added and a homogeneous mixture prepared before use.

The dyeing compositions according to the invention may comprise any active ingredients, additives or adjuvants known for such preparations, like surfactants, solvents, bases, acids, perfumes, polymeric adjuvants, thickeners and light stabilisers.

The following adjuvants are preferably used in the hair dyeing compositions of the present invention:
non-ionic polymers, for example vinylpyrrolidone/vinyl acrylate copolymers, polyvinylpyrrolidone and vinylpyrrolidone/vinyl acetate copolymers and polysiloxanes;
cationic polymers, such as quaternised cellulose ethers, polysiloxanes having quaternary groups, dimethyldiallylammonium chloride polymers, copolymers of dimethyldiallylammonium chloride and acrylic acid, as available commercially under the name Merquat® 280 and the use thereof in hair dyeing as described, for example, in DE-A-4 421 031, especially p. 2, l. 20 to 49, or EP-A-953 334, especially p. 27, l. 17 to p. 30, l. 11;
acrylamide/dimethyldiallylammonium chloride copolymers, diethyl-sulfate-quaternised dimethylaminoethyl methacrylate/vinylpyrrolidone copolymers, vinylpyrrolidone/imidazolinium methochloride copolymers;
quaternised polyvinyl alcohol:
zwitterionic and amphoteric polymers, such as acrylamido-propyltrimethylammonium chloride/acrylate copolymers and octylacrylamide/methyl methacrylate/tert-butylaminoethyl methacrylate/2-hydroxypropyl methacrylate copolymers;
anionic polymers, such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butyl acrylamide terpolymers;
thickeners, such as agar, guar gum, alginates, xanthan gum, gum arabic, karaya gum, locust bean flour, linseed gums, dextrans, cellulose derivatives, e.g. methyl cellulose, hydroxyalkyl cellulose and carboxymethyl cellulose, starch fractions and derivatives, such amylose, amylopectin and dextrins, clays, e.g. bentonite or fully synthetic hydrocolloids such as, for example, polyvinyl alcohol;
structuring agents, such as glucose and maleic acid;
hair-conditioning compounds, such as phospholipids, for example soya lecithin, egg lecithin, cephalins, silicone oils, and conditioning compounds, such as those described in DE-A-19 729 080, especially p. 2, l. 20 to 49, EP-A-834 303, especially p. 2, l. 18-p. 3, l. 2, or EP-A-312 343, especially p. 2, l. 59-p. 3, l. 11;
protein hydrolysates, especially elastin, collagen, keratin, milk protein, soya protein and wheat protein hydrolysates, condensation products thereof with fatty acids and also quaternised protein hydrolysates;
perfume oils, dimethyl isosorbitol and cyclodextrins,
solubilisers, such as ethanol, isopropanol, ethylene glycol, propylene glycol, glycerol and diethylene glycol,
anti-dandruff active ingredients, such as piroctones, olamines and zinc Omadine,
substances for adjusting the pH value;
panthenol, pantothenic acid, allantoin, pyrrolidonecarboxylic acids and salts thereof, plant extracts and vitamins;
cholesterol;
light stabilisers and UV absorbers as listed in Table below:

TABLE 1

UV absorbers which may be use in the dyeing compositions of the present invention

| No. | Chemical Name | CAS No. |
|---|---|---|
| 1 | (+/−)-1,7,7-trimethyl-3-[(4-methylphenyl)methylene]bicyclo-[2.2.1]heptan-2-one | 36861-47-9 |
| 2 | 1,7,7-trimethyl-3-(phenylmethylene)bicyclo[2.2.1]heptan-2-one | 15087-24-8 |

TABLE 1-continued

UV absorbers which may be use in the dyeing compositions of the present invention

| No. | Chemical Name | CAS No. |
|---|---|---|
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone; | 131-57-7 |
| 7 | 2,2'-dihydroxy-4,4'-dimethoxybenzophenone | 131-54-4 |
| 8 | 2,2'-Dihydroxy-4-methoxybenzophenone | 131-53-3 |
| 9 | 1-[4-(1,1-dimethylethyl)phenyl]-3-(4-methoxyphenyl)propane-1,3-dione | 70356-09-1 |
| 10 | 3,3,5-Trimethyl cyclohexyl-2-hydroxy benzoate | 118-56-9 |
| 11 | Isopentyl p-methoxycinnamate | 71617-10-2 |
| 12 | Menthyl-o-aminobenzoate | 134-09-8 |
| 13 | Menthyl salicylate | 89-46-3 |
| 14 | 2-Ethylhexyl 2-cyano,3,3-diphenylacrylate | 6197-30-4 |
| 15 | 2-ethylhexyl 4-(dimethylamino)benzoate | 21245-02-3 |
| 16 | 2-ethylhexyl 4-methoxycinnamate | 5466-77-3 |
| 17 | 2-ethylhexyl salicylate | 118-60-5 |
| 18 | Benzoic acid, 4,4',4''-(1,3,5-triazine-2,4,6-triyltriimino)tris-, tris(2-ethylhexyl)ester; 2,4,6-Trianilino-(p-carbo-2'-ethylhexyl-1'-oxi)-1,3,5-triazine | 88122-99-0 |
| 19 | Benzoic acid, 4-amino-, ethyl ester, polymer with oxirane | 113010-52-9 |
| 20 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 21 | Triethanolamine salicylate | 2174-16-5 |
| 22 | 2,2'-Methylene-bis-[6-(2H-benzotriazol-2-yl)-4-(1,1,3,3-tetramethyl-butyl)-phenol] | 103597-45-1 |
| 23 | 2,4-bis{[4-(2-ethylhexyloxy)-2-hydroxy]-phenyl}-6-(4-methoxyphenyl)-(1,3,5)-triazine (Tinosorb S) | 187393-00-6 |
| 24 | Benzoic acid, 4,4'-[[6-[[4-[[(1,1-dimethylethyl)amino]carbonyl]-phenyl]amino]1,3,5-triazine-2,4-diyl]diimino]bis-, bis(2-ethylhexyl)-ester | 154702-15-5 |
| 25 | Phenol, 2-(2H-benzotriazol-2-yl)-4-methyl-6-[2-methyl-3-[1,3,3,3-tetramethyl-1-[(trimethylsilyl)oxy]disiloxanyl]propyl]- | 155633-54-8 |
| 26 | Dimethicodiethylbezalmalonate | 207574-74-1 |
| 27 | Benzoic acid, 2-[4-(diethylamino)-2-hydroxybenzoyl]-, hexyl ester | 302776-68-7 |
| 28 | 1,3,5-Triazine, 2,4,6-tris(4-methoxyphenyl)- | 7753-12-0 |
| 29 | 1,3,5-Triazine, 2,4,6-tris[4-[(2-ethylhexyl)oxy]phenyl]- | 208114-14-1 |
| 30 | 2-Propenoic acid, 3-(1H-imidazol-4-yl)- | 104-98-3 |
| 31 | Benzoic acid, 2-hydroxy-, [4-(1-methylethyl)phenyl]methyl ester | 94134-93-7 |
| 32 | 1,2,3-Propanetriol, 1-(4-aminobenzoate) | 136-44-7 |
| 33 | Benzeneacetic acid, 3,4-dimethoxy-a-oxo- | 4732-70-1 |
| 34 | 2-Propenoic acid, 2-cyano-3,3-diphenyl-, ethyl ester | 5232-99-5 |
| 35 | Anthralinic acid, p-menth-3-yl ester | 134-09-8 |
| 36 | 1,3,5-Triazine-2,4,6-triamine, N,N'-bis[4-[5-(1,1-dimethylpropyl)-2-benzoxazolyl]phenyl]-N''-(2-ethylhexyl)- or Uvasorb K2A | 288254-16-0 |
| 37 | 2-Hydroxy-4-methoxy benzophenone-5-sulphonic acid | 4065-45-6 |
| 38 | Alpha-(2-oxoborn-3-ylidene)toluene-4-sulphonic acid and its salts | 56039-58-8 |
| 39 | Methyl N,N,N-trimethyl-4-[(4,7,7-trimethyl-3-oxobicyclo[2,2,1]hept-2-ylidene)methyl]anilinium sulphate; | 52793-97-2 |
| 40 | 4-aminobenzoic acid | 150-13-0 |
| 41 | 2-phenyl-1H-benzimidazole-5-sulphonic acid | 27503-81-7 |
| 42 | 3,3'-(1,4-phenylenedimethylene)bis[7,7-dimethyl-2-oxo-bicyclo[2.2.1]heptane-1-methanesulfonic acid] | 90457-82-2 |
| 43 | 1H-Benzimidazole-4,6-disulfonic acid, 2,2'-(1,4-phenylene)bis-, disodium salt | 180898-37-7 |
| 44 | Benzenesulfonic acid, 3-(2H-benzotriazol-2-yl)-4-hydroxy-5-(1-methylpropyl)-, monosodium salt | 92484-48-5 |
| 45 | 1-Dodecanaminium, N-[3-[[4-(dimethylamino)benzoyl]amino]-propyl]N,N-dimethyl-, salt with 4-methylbenzenesulfonic acid (1:1) | 156679-41-3 |
| 46 | 1-Propanaminium, N,N,N-trimethyl-3-[(1-oxo-3-phenyl-2-propenyl)-amino]-, chloride | 177190-98-6 |
| 47 | 1H-Benzimidazole-4,6-disulfonic acid, 2,2'-(1,4-phenylene)bis- | 170864-82-1 |
| 48 | 1-Propanaminium, 3-[[3-[3-(2H-benzotriazol-2-yl)-5-(1,1-dimethyl-ethyl)-4-hydroxyphenyl]-1-oxopropyl]amino]-N,N-diethyl-N-methyl-, methyl sulfate (salt) | 340964-15-0 |
| 49 | 2,2'-bis(1,4-phenylene)-1H-benzimidazole-4,6-disulphonic acid mono sodium salt or Disodium phenyl dibenzimidazole tetrasulfonate or Neoheliopan AP | 349580-12-7, |

The use of UV absorbers can effectively protect natural and dyed hair from the damaging rays of the sun and increase the wash fastness of dyed hair.

Furthermore, the following UV absorbers or combinations may be used in the dyeing compositions according to the invention:

cationic benzotriazole UV absorbers as for example described in WO 01/36396 especially on p. 1, l. 20 to p. 2, l. 24, and preferred on p. 3 to 5, and on p. 26 to 37;

cationic benzotriazole UV in combination with antioxidants as described in WO 01/36396, especially on p. 11, l. 14 to p. 18;

UV absorbers in combination with antioxidants as described in U.S. Pat. No. 5,922,310, especially in col 2, l. 1 to 3;

UV absorbers in combination with antioxidants as described in U.S. Pat. No. 4,786,493, especially in col 1, 42 to col 2, l. 7, and preferred in col 3, 43 to col 5, l. 20;

combination of UV absorbers as described in U.S. Pat. No. 5,830,441, especially in col 4, l. 53 to 56;

combination of UV absorbers as described in WO 01/36396, especially on p. 11, l. 9 to 13; or triazine derivatives as described in WO 98/22447, especially on p. 1, l. 23 to p. 2, l. 4, and preferred on p. 2, l. 11 to p. 3, l. 15 and most preferred on p. 6 to 7, and 12 to 16.

Suitable cosmetic preparations may usually contain 0.05 to 40% by weight, preferably from 0.1 to 20% by weight, based on the total weight of the composition, of one or more UV absorbers;

consistency regulators, such as sugar esters, polyol esters or polyol alkyl ethers;

fats and waxes, such as spermaceti, beeswax, montan wax, paraffins, fatty alcohols and fatty acid esters;

fatty alkanolamides;

polyethylene glycols and polypropylene glycols having a molecular weight of from 150 to 50 000, for example such as those described in EP-A-801 942, especially p. 3, l. 44 to 55, complexing agents, such as EDTA, NTA and phosphonic acids, swelling and penetration substances, such as polyols and polyol ethers, as listed extensively, for example, in EP-A-962 219, especially p. 27, l. 18 to 38, for example glycerol, propylene glycol, propylene glycol monoethyl ether, butyl glycol, benzyl alcohol, carbonates, hydrogen carbonates, guanidines, ureas and also primary, secondary and tertiary phosphates, imidazoles, tannins, pyrrole;

opacifiers, such as latex;

pearlising agents, such as ethylene glycol mono- and di-stearate;

propellants, such as propane-butane mixtures, $N_2O$, dimethyl ether, $CO_2$ and air;

antioxidants;

sugar-containing polymers, as described in EP-A-970 687, especially p. 28, l. 17 to p. 29, l. 23;

quaternary ammonium salts, as described in WO 00/10517, especially p. 44, l. 16 to p. 46, l. 23.

Bacteria inhibiting agents, like preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations;

The dyeing compositions according to the present invention generally comprise at least one surfactant. Suitable surfactants are zwitterionic or ampholytic, or more preferably anionic, non-ionic and/or cationic surfactants.

Suitable anionic surfactants in the dyeing compositions according to the present invention include all anionic surface-active substances that are suitable for use on the human body. Such substances are characterised by an anionic group that imparts water solubility, for example a carboxylate, sulfate, sulfonate or phosphate group, and a lipophilic alkyl group having approximately 10 to 22 carbon atoms. In addition, glycol or polyglycol ether groups, ester, ether and amide groups and also hydroxy groups may be present in the molecule. The following are examples of suitable anionic surfactants, each in the form of sodium, potassium or ammonium salts or mono-, di- or tri-alkanolammonium salts having 2 or 3 carbon atoms in the alkanol group:

linear fatty acids having 10 to 22 carbon atoms (soaps), ether carboxylic acids of formula $R-O-(CH_2-CH_2-O)_x-CH_2-COOH$, in which R is a l.ar alkyl group having 10 to 22 carbon atoms and x=0 or from 1 to 16, acyl sarcosides having 10 to 18 carbon atoms in the acyl group, acyl taurides having 10 to 18 carbon atoms in the acyl group, acyl isothionates having 10 to 18 carbon atoms in the acyl group, sulfosuccinic mono- and di-alkyl esters having 8 to 18 carbon atoms in the alkyl group and sulfosuccinic monoalkylpolyoxyethyl esters having 8 to 18 carbon atoms in the alkyl group and from 1 to 6 oxyethyl groups, linear alkane sulfonates having 12 to 18 carbon atoms, linear $\alpha$-olefin sulfonates having 12 to 18 carbon atoms, $\alpha$-sulfo fatty acid methyl esters of fatty acids having 12 to 18 carbon atoms, alkyl sulfates and alkyl polyglycol ether sulfates of formula $R'-O(CH_2-CH_2-O)_{x'}-SO_3H$, in which R' is a preferably l.ar alkyl group having 10 to 18 carbon atoms and x'=0 or from 1 to 12, mixtures of surface-active hydroxysulfonates according to DE-A-3 725 030, especially p. 3, l. 40 to 55, sulfated hydroxyalkylpolyethylene and/or hydroxyalkylenepropylene glycol ethers according to DE-A-3 723 354, especially p. 4, l. 42 to 62, sulfonates of unsaturated fatty acids having 12 to 24 carbon atoms and 1 to 6 double bonds according to DE-A-3 926 344, especially p. 2, l. 36 to 54, esters of tartaric acid and citric acid with alcohols which are addition products of approximately from 2 to 15 molecules of ethylene oxide and/or propylene oxide with fatty alcohols having from 8 to 22 carbon atoms, or anionic surfactants, as described in WO 00/10518, especially p. 45, l. 11 to p. 48, l. 3.

Preferred anionic surfactants are alkyl sulfates, alkyl polyglycol ether sulfates and ether carboxylic acids having 10 to 18 carbon atoms in the alkyl group and up to 12 glycol ether groups in the molecule, and also especially salts of saturated and especially unsaturated $C_8$-$C_{22}$carboxylic acids, such as oleic acid, stearic acid, isostearic acid and palmitic acid.

Surface-active compounds that carry at least one quaternary ammonium group and at least one $-COO^-$ or $-SO_3^-$ group in the molecule are terminated zwitterionic surfactants. Preference is given the so-called betaines, such as the N-alkylN,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazol. having from 8 to 18 carbon atoms in the alkyl or acyl group and also cocoacylaminoethylhydroxyethylcarboxymethyl glycinate. A preferred zwitterionic surfactant is the fatty acid amide derivative known by the CTFA name cocoamidopropyl betaine.

Ampholytic surfactants are surface-active compounds that, in addition to a $C_8$-$C_{18}$-alkyl or -acyl group and contain at least one free amino group and at least one —COOH or —$SO_3H$ group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group. Ampholytic surfactants to which special preference is given are N-cocoalkylaminopropionate, cocoacylaminoethylaminopropionate and $C_{12}$-$C_{18}$acylsarcosine.

Suitable non-ionic surfactants are described in WO 00/10519, especially p. 45, l. 11 to p. 50, l. 12. Non-ionic surfactants contain as hydrophilic group, for example, a polyol group, a polyalkylene glycol ether group or a combination of polyol and polyglycol ether groups. Such compounds are, for example:
- addition products of 2 to 30 mol of ethylene oxide and/or 0 to 5 mol of propylene oxide with l.ar fatty alcohols having 8 to 22 carbon atoms, with fatty acids having 12 to 22 carbon atoms and with alkylphenols having 8 to 15 carbon atoms in the alkyl group,
- $C_{12}$-$C_{22}$ fatty acid mono- and di-esters of addition products of 1 to 30 mol of ethylene oxide with glycerol,
- $C_8$-$C_{22}$alkyl-mono- and -oligo-glycosides and ethoxylated analogues thereof,
- addition products of 5 to 60 mol of ethylene oxide with castor oil and hydrogenated castor oil,
- addition products of ethylene oxide with sorbitan fatty acid esters,
- addition products of ethylene oxide with fatty acid alkanolamides.

The surfactants which are addition products of ethylene and/or propylene oxide with fatty alcohols or derivatives of such addition products may either be products having a "normal" homologue distribution or products having a restricted homologue distribution. "Normal" homologue distribution are mixtures of homologues obtained in the reaction of fatty alcohol and alkylene oxide using alkali metals, alkali metal hydroxides or alkali metal alcoholates as catalysts. Restricted homologue distributions, on the other hand, are obtained when, for example, hydrotalcites, alkali metal salts of ether carboxylic acids, alkali metal oxides, hydroxides or alcoholates are used as catalysts.

The use of products having restricted homologue distribution may be preferred.

Examples of cationic surfactants that can be used in the dyeing compositions according to the invention are especially quaternary ammonium compounds. Preference is given to ammonium halides, such as alkyltrimethylammonium chlorides, dialkyldimethylammonium chlorides and trialkylmethylammonium chlorides, for example cetyltrimethylammonium chloride, stearyltrimethylammonium chloride, distearyldimethyl-lammonium chloride, lauryldimethylammonium chloride, lauryldimethylbenzylammonium chloride and tricetylmethylammonium chloride. Further cationic surfactants that can be used in accordance with the invention are quaternised protein hydrolysates.

Also suitable are cationic silicone oils, such as, for example, the commercially available products Q2-7224 (manufacturer: Dow Corning; a stabilised trimethylsilylamodimethicone), Dow Corning 929 emulsion (comprising a hydroxylamino-modified silicone, which is also referred to as amodimethicone), SM-2059 (manufacturer: General Electric), SLM-55067 (manufacturer: Wacker) and also Abil®-Quat 3270 and 3272 (manufacturer: Th. Goldschmidt; diquaternary polydimethylsiloxanes, quaternium-80), or silicones, as described in WO 00/12057, especially p. 45, l. 9 to p. 55, l. 2.

Alkylamidoamines, especially fatty acid amidoamines, such as the stearylamidopropyldi-methylamine obtainable under the name Tego Amid®18 are also preferred as surfactants in the present dyeing compositions. They are distinguished not only by a good conditioning action but also especially by their good biodegradability.

An example of a quaternary sugar derivative that can be used as cationic surfactant is the commercial product Glucquat® 100, according to CTFA nomenclature a "lauryl methyl gluceth-10 hydroxypropyl dimonium chloride".

The alkyl-group-containing compounds used as surfactants may be single substances, but the use of natural raw materials of vegetable or animal origin is generally preferred in the preparation of such substances, with the result that the substance mixtures obtained have different alkyl chain lengths according to the particular starting material used.

A further embodiment of the present invention relates to the dyeing of keratin-containing fibers. The processes comprises
(a) treating the keratin-containing fiber with at least one dye of the present invention and
(b) leaving the fiber to stand and then rinsing the fiber.

The dyes of the present invention are suitable for all-over dyeing of the hair, that is to say when dyeing the hair on a first occasion, and also for re-dyeing subsequently, or dyeing of locks or parts of the hair.

The dyes of the present invention are applied on the hair for example by massage with the hand, a comb, a brush, or a bottle, or a bottle, which is combined with a comb or a nozzle.

In the processes for dyeing according to the invention, whether or not dyeing is to be carried out in the presence of a further dye will depend upon the color shade to be obtained.

Further preferred is a process for dyeing keratin-containing fibers which comprises treating the keratin-containing fiber with at least one dye of the present invention, a base and an oxidizing agent.

A preferred embodiment for dyeing keratin-containing fibers, in particular human hair, with a dye of the present invention and an oxidizing agent, comprises
$a_1$) treating the keratin-containing fiber with the oxidizing agent, which optionally contains at least one dye of the present invention,
$b_1$) treating the keratin-containing fiber with an oxidizing agent free composition, which optionally contains at least one dye of the present invention; or alternatively
$a_2$) treating the keratin-containing fiber with an oxidizing agent free composition, which optionally contains at least one dye of the present invention;
$b_2$) treating the keratin-containing fiber with an oxidizing agent, which optionally contains least one dye of the present invention,
with the proviso that at least in one of the process steps $a_1$), $a_2$), $b_1$) or $b_2$) a dye according to the invention is present.

In general, the oxidizing agent containing composition is left on the fiber for 0 to 15 minutes, in particular for 0 to 5 minutes at 15 to 45° C.

The oxidizing agent free composition usually comprises customary adjuvants and additives. Preferred are those, which are described in German Patent Application, in col 3, l. 17 to l. 41.

In general, the dye of the present invention and the oxidizing agent free composition are left on the fiber for 5 to 45 minutes, in particular for 10 to 25 minutes at 15 to 50° C.

One preferred embodiment of the process is to wash the hair after dyeing with a shampoo and/or a weak acid, such as citric acid or tartrate acid.

The dyes of the present invention which are stable to reduction can be stored together with the oxidizing agent free compositions and may be applied as a single composition.

Advantageously the compositions comprising a dye of the present invention which are not stable to reduction are prepared with the oxidizing agent free composition just before the dyeing process.

In a further embodiment, the dye of the present invention and the oxidizing agent free composition may be applied simultaneously or in succession.

Customarily, the oxidizing agent containing composition is evenly applied in a sufficient amount related to the amount of hair, usually in amounts of 30 to 200 g.

Oxidizing agents are for example persulfate or dilute hydrogen peroxide solutions, hydrogen peroxide emulsions or hydrogen peroxide gels, alkal. earth metal peroxides, organic peroxides, such as urea peroxides, melamine peroxides, or alkalimetalbromat fixations are also applicable if a shading powder on the basis of semi-permanent, direct hair dyes is used.

Further preferred oxidizing agents are
  oxidizing agents to achieve lightened coloration, as described in WO 97/20545, especially p. 9, l. 5 to 9,
  oxidizing agents in the form of permanent-wave fixing solution, as described in DE-A-19 713 698, especially p. 4, l. 52 to 55, and l. 60 and 61 or EP-A-1062940, especially p. 6, l. 41 to 47 (and in the equivalent WO 99/40895).

Most preferred oxidizing agent is hydrogen peroxide, preferably used in a concentration from about 2 to 30%, more preferably about 3 to 20% by, and most preferably from 6 to 12% by weight the corresponding composition.

The oxidizing agents may be present in the dyeing compositions according to the invention preferably in an amount from 0.01% to 6%, especially from 0.01% to 1%, based on the total dyeing composition.

In general, the dyeing with an oxidative agent is carried out in the presence of a base, for example ammonia, alkali metal carbonates, earth metal (potassium or lithium) carbonates, alkanol amines, such as mono-, di- or triethanolamine, alkali metal (sodium) hydroxides, earth metal hydroxides or compounds of the formula

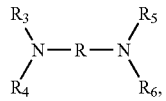

wherein
R is a propylene residue, which may be substituted with OH or $C_1$-$C_4$alkyl,
$R_3$, $R_4$, $R_5$ and $R_6$ are independently or dependently from each other hydrogen, $C_1$-$C_4$alkyl or hydroxy-($C_1$-$C_4$)alkyl.

The pH-value of the oxidizing agent containing composition is usually about 2 to 7, and in particular about 2 to 5.

One preferred method of applying formulations-comprising the dyes of the present invention on the keratin-containing fiber, preferably the hair is by using a multi-compartment dyeing device or "kit" or any other multi-compartment packaging system, as described for example in WO 97/20545 on p. 4, l. 19 to l. 27.

The first compartment contains for example at least one dye of the present invention and optionally further direct dyes and a basifying agent, and in the second compartment an oxidizing agent; or in the first compartment at least one dye of the present invention and optionally further direct dyes, in the second compartment a bsifiying agent and in the third compartment an oxidizing agent.

Preferably, a ready-to-use composition is prepared according to a first preferred embodiment by a process which comprises a preliminary step which involves separately storing, on the one hand, a composition (A) comprising, in a medium which is suitable for dyeing, at least one developer compound, especially selected from para-phenylenediamines and bis(phenyl)-alkylenediamines, and the acid-addition salts thereof, at least one coupler, especially selected from meta-phenylenediamines and the acid-addition salts thereof, and at least one dye of the present invention, on the other hand, a composition (B) containing, in a medium which is suitable for dyeing, at least one oxidizing agent and mixing (A) and (B) together immediately before applying this mixture to the keratin-containing fibers.

According to a second preferred embodiment for the preparation of the ready-to-use dye composition, the process includes a preliminary step which involves separately storing, on the one hand, a composition (A) comprising, in a medium which is suitable for dyeing, at least one developer compound, especially selected from para-phenylenediamines and bis(phenyl)alkylenediamines, and the acid-addition salts thereof, at least one coupler compound, especially selected from meta-phenylenediamines and the acid-addition salts thereof; on the other hand, a composition (A') comprising, in a medium which is suitable for dyeing, at least one dye of the present invention, and finally, a composition (B) containing, in a medium which is suitable for dyeing, at least one oxidizing agent as defined above, and mixing them together at the time of use immediately before applying this mixture to the keratin-containing fibers.

The composition (A') used according to this second embodiment may optionally be in powder form, the cationic dye(s) of the present invention (themselves) constituting, in this case, all of the composition (A') or optionally being dispersed in an organic and/or inorganic pulverulent excipient.

When present in the composition A', the organic excipient may be of synthetic or natural origin and is selected in particular from crosslinked and non-crosslinked synthetic polymers, polysaccharides such as celluloses and modified or unmodified starches, as well as natural products such as sawdust and plant gums (guar gum, carob gum, xanthan gum, etc.).

When present in the composition (A'), the inorganic excipient may contain metal oxides such as titanium oxides, aluminium oxides, kaolin, talc, silicates, mica and silicas.

A very suitable excipient in the dyeing compositions according to the invention is sawdust.

The powdered composition (A') may also contain binders or coating products in an amount which preferably does not exceed approximately 3% by weight relative to the total weight of composition (A'). These binders are preferably selected from oils and liquid fatty substances of inorganic, synthetic, animal or plant origin.

The composition (A') may optionally contain other adjuvants, in powdered form, in particular surfactants of any kind, hair conditioners such as, for example, cationic polymers, etc.

Generally the hair is rinsed after treatment with the dyeing solution and/or permanent-wave solution.

A further preferred embodiment of the present invention relates to a method of dyeing hair with oxidative dyes, which comprises a. mixing at least one dye of the invention and optionally at least one coupler compound and at least one developer compound, and an oxidizing agent, which optionally contains at least one further dye, and b. contacting the keratin-containing fibers with the mixture as prepared in step a.

For adjusting the pH-value organic or inorganic acids, as for example described in DE 199 59 479, col 3, l. 46 to l. 53 are suitable.

Furthermore, the present invention relates to a process of dyeing of keratin-containing fibers of the dyes of the present invention with autooxidable compounds and optionally further dyes.

The process comprises a. mixing at least one autooxidable compound and at least one developer compound and at least one dye of the present invention and optionally further dyes, and b. treating the keratin-containing fiber with the mixture prepared in step a.

Furthermore, the present invention relates to a process for dyeing keratin-containing fibers with the dyes of the present invention and capped diazotised compounds, which comprises, a. treating the keratin-containing fibers under alkaline conditions with at least one capped diazotised compound and a coupler compound, and optionally a developer compound ad optionally an oxidizing agent, and optionally in the presence of a further dye, and optionally with at least one dye of the present invention, and b. adjusting the pH in the range of 6 to 2 by treatment with an acid, optionally in the presence of a further dye, and optionally at least one dye of the present invention, with the proviso that at least in one step a. or b. at least one dye of the invention is present.

The capped diazotised compound and coupler compound and optionally the oxidizing agent and developer compound can be applied in any desired order successively or simultaneously.

Preferably, the capped diazotised compound and the coupler compound are applied simultaneously, in a single composition.

"Alkaline conditions" denotes a pH in the range from 8 to 10, preferably 9-10, especially 9.5-10, which are achieved by the addition of bases, for example sodium carbonate, ammonia or sodium hydroxide.

The bases may be added to the hair, to the dye precursors, the capped diazotised compound and/or the water-soluble coupling component, or to the dyeing compositions comprising the dye precursors.

Acids are for example tartaric acid or citric acid, a citric acid gel, a suitable buffer solution with optionally an acid dye.

The ratio of the amount of alkal. dyeing composition applied in the first stage to that of acid dyeing composition applied in the second stage is preferably about from 1:3 to 3:1, especially about 1:1.

The alkaline dyeing compositions of step a. and the acid dyeing compositions of step b. are left on the fiber for 5 to 60 minutes at 15 to 45° C., in particular for 5 to 45 minutes at 20 to 30° C.

Furthermore, the present invention relates to a process for dyeing keratin-containing fibers with a dye of the present invention and at least one acid dye.

Preparation

The present invention further pertains to a process for the preparation of a highly crosslinked polysiloxane, characterized in that a silane reaction mixture comprising a monomer of the formula (III)

$$X_3Si\text{-}T\text{-}Dye \quad (III),$$

wherein X is a leaving group such as halogen or alkoxy, especially Cl or $C_1$-$C_8$alkoxy; T is a direct bond or an organic spacer group such as $C_1$-$C_{18}$alkylene; $C_2$-$C_{12}$alkenylene; $C_5$-$C_{10}$cycloalkylene; $C_5$-$C_{10}$arylene; —$C_5$-$C_{10}$arylene-($C_1$-$C_{10}$alkylene)-, which may be end-capped towards the linkage to Dye by CO, COO, $NR^1$, $CONR^1$, $NR^1CONR^1$, CS, CSS, $CSNR^1$, $NR^1CSNR^1$, O, S, SO, —$SO_2$—, $C_5$-$C_{10}$cycloalkylene, $C_5$-$C_{10}$arylene; or T is $C_3$-$C_{15}$alkylene interrupted, and optionally end-capped towards the linkage to Dye, by CO, COO, $NR^1$, $CONR^1$, $NR^1CONR^1$, CS, CSS, $CSNR^1$, $NR^1CSNR^1$, O, S, SO, —$SO_2$—, $C_5$-$C_{10}$cycloalkylene, $C_5$-$C_{10}$arylene; or is CO—; —($CH_2CH_2$—O)$_{1\text{-}5}$—; COO; $N(R^1)$; $CON(R^1)$; O; S; SO; —$SO_2$—;

$R^1$ is hydrogen; unsubstituted or substituted, straight-chain or branched, monocyclic or polycyclic, interrupted or uninterrupted $C_1$-$C_{14}$alkyl; $C_2$-$C_{14}$alkenyl; $C_6$-$C_{10}$aryl; $C_6$-$C_{10}$aryl-$C_1$-$C_{10}$alkyl; or $C_5$-$C_{10}$alkyl($C_5$-$C_{10}$aryl);

and Dye is a residue of an organic dye, is subjected to polycondensation. Consequently, the invention provides a highly crosslinked polysiloxane dye which is obtainable by the above process (corresponding to a modified Stöber Process).

Besides educt monomers of the formula (III), further monomers may be added in order to modify the structure of the polysiloxane particle, e.g. the chromophor concentration within the particle, the degree of crosslinking or, if added in a second step e.g. as a polymerization regulator, size and/or surface properties of the particle.

Thus, the initial reaction mixture may additionally contain one or more further copolymerizable silane monomers, such as those of the formulae

$$X_3Si\text{-}T\text{-}H \quad (IIIa),$$

$$X_3Si\text{-}T\text{-}A \quad (IIIb),$$

$$X_2Si(R^2)\text{-}T\text{-}Dye \quad (IV)$$

$$X_2Si(R^2)\text{-}T\text{-}H \quad (IVa),$$

$$X_2Si(R^2)\text{-}T\text{-}A \quad (IVb),$$

wherein

X, T and Dye are as explained above,

A is a cationic moiety other than the one of an organic dye, whose charge is balanced by a suitable anion, $R^2$ is $C_1$-$C_8$alkyl or -T-Dye or -T-H or -T-A;

where the monomers containing no chromophor (organic dye radical) usually may be contained in an amount of up to 90 mol-% of the total silane monomers in the initial reaction mixture;

or one or more of the above monomers of the formulae (IIIa), (IIIb), (IV), (IVa), (IVb), or of the formulae

$$X_3Al \quad (Ia),$$

$$X_4Si \quad (Ib),$$

$$X_2Al\text{-}T\text{-}H \quad (IIIc),$$

$$X\text{—}Al(R^2)\text{-}T\text{-}H \quad (IVc),$$

$$XSi(R^2)_2\text{-}T\text{-}Dye \quad (V),$$

$$XSi(R^2)_2\text{-}T\text{-}H \quad (Va),$$

$$XSi(R^2)_2\text{-}T\text{-}A \quad (Vb),$$

is added to the reaction mixture after commence of the polycondensation reaction.

If monomers other than of formula III are used, these are preferably added after allowing the condensation of the formula III monomers to start, e.g. after about 10-70%, or about 50%, of the initial monomers have reacted or, in some cases, 5-70% of the condensation by-products (such as alcohol or halide) have formed (thus obtaining an extended particle). A further variant is addition of one or more of these monomers (i.e. any monomer of formulae Ia, Ib, IIIa-c, IVa-c, V, Va-b) after completion of the major part of the reaction, e.g. after 90%, especially 99%, of the silane monomers initially present in the reaction mixture have been reacted (thus forming a shell around the core particle).

Addition of a monomer of the type of formulae (V), (Va) and/or (Vb) during the end phase of the polycondensation reaction, or after the end of the polycondensation reaction, may lead to a passivation of reactive sites on the dye particle obtained.

Examples for such modifying agents are trialkoxyaluminum or tetraalkoxysilane as efficient shell formers, or trimethylalkoxysilane as a passivating reagent, introducing one or more non-chromophor containing layers on the surface of the particle, while retaining its color.

The cationic moiety other than the one of an organic dye A is preferably an ammonium group e.g. of the formula —N$^+$(R$^{11}$)(R$^{12}$)(R$^{13}$) wherein each of R$^{11}$, R$^{12}$, R$^{13}$, independently, are selected from H; $C_1$-$C_{18}$alkyl; $C_1$-$C_{18}$alkanoyl; or $C_3$-$C_{18}$alkyl or $C_2$-$C_{18}$alkanoyl interrupted by CO, COO, NR$^1$, CONR$^1$, O, S, SO, —SO$_2$—, $C_5$-$C_{10}$cycloalkylene, $C_5$-$C_{10}$arylene; or 2 or 3 of the residues R$^{11}$, R$^{12}$, R$^{13}$ are interconnected to form a heterocyclic, e.g. $C_1$-$C_{10}$heterocyclic, moiety such as pyridinium, piperidinium, imidazolinium.

The polycondensation reaction usually takes place in presence of a proton donor and a suitable solvent, preferably in the presence of water, an aqueous acid or an aqueous base such as aqueous HCl, H$_2$SO$_4$, acetic, phosphoric acid, ammonia, alkaline or alkaline earth hydroxide etc., with or without addition of a catalyst. Further solvents may be added, especially water-miscible ones such as lower alcohols, inter alia to improve solubility of the chromophor-containing educts. While the reaction temperature is not critical, it is often kept within the range of 0 to about 120° C., e.g. room temperature to the boiling/refluxing temperature of the reaction mixture, for reasons of practicability.

Recovery of the particles may be facilitated by addition of a further organic solvent showing miscibility with water, acid and/or base used, which may be followed by steps like filtration, solvent removal, washing and/or drying commonly known in the art.

As noted above, the organic dye moiety Dye is formed from known dyes by abstraction of a hydrogen atom. Preferably, the organic dye used for preparing the above compound of the formula (III), (IV) or (V) has a functional group selected from electrophilic groups such as halide, tosylate, mesylate, methoxy, acid chloride, sulfonyl chloride, epoxides, anhydride; and nucleophilic groups such as amine, hydroxyl and thiol, which is reacted with a correspondingly substituted silane counterpart to obtain the compound of the formula (III), (IV) or (V).

The examples which follow illustrate the invention in more detail, without restriciting the scope to said examples only. Where alkyl radicals having more than three carbon atoms are referred to in the examples without any mention of specific isomers, the n-isomers are meant in each case. In the examples as well as in other parts of this specification, quantities of solutions and liquids are usually given by volume, all other amounts by weight, if not stated otherwise. Parts and percentages are, as in the remainder of this specification and in the claims, by weight, unless stated otherwise. Room temperature denotes a temperature in the range 20-25° C.; overnight a time period in the range 12-16 hours. Migration tests are carried out in accordance with DIN 53775-3. Abbreviations:

DLS Dynamic light scattering;
TGA ThermoGravimetric Analysis;
TEM Transmission Electron Microscopy;
exc. excess (amount of reagent).

SYNTHETIC EXAMPLES

Example A1

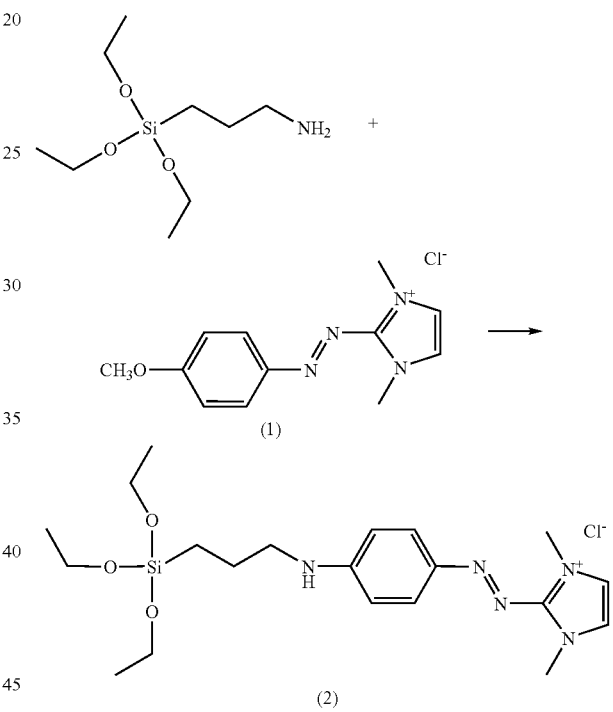

A mixture of (3-aminopropyl)triethoxysilane (10.0 g), compound 1 (11.44 g) and ethanol (200 ml) is heated to reflux overnight. The mixture is then cooled to room temperature and the solvents removed under vacuum to give the product (compound 2) as a dark red solid, which is used without further purification.

Example A2

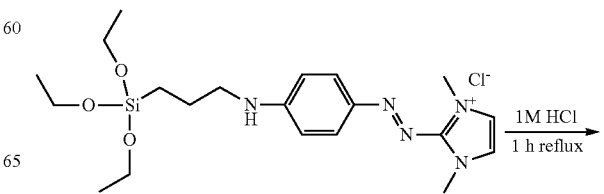

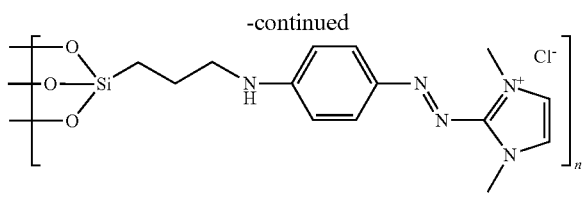

9.16 g of the compound 2 is heated to reflux in aqueous HCl (1M) for one hour. The reaction mixture is cooled to room temperature, the precipitate is collected by filtration and dried at 40° C. under vacuum to yield 6.71 g of a dark red powder.

DLS shows monodisperse particles of 200 nm diameter. Elemental analysis shows 67.13% from C, H and N combined. TGA shows loss of 75.584%, corresponding to the organic material.

Examples A3-A6

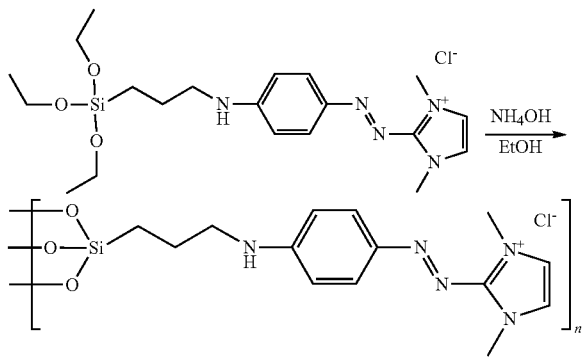

Compound 2 (1.0 g) is dissolved in ethanol (10 ml), and then ammonium hydroxide (25% aqueous solution, 1.0 ml) is added and the mixture stirred overnight at room temperature. The volume of the mixture is doubled by the addition of acetone, and the formed precipitate is filtered off and washed several times with more acetone followed by diethyl ether. This gives the polymeric material as a dark red coloured solid (0.63 g).

Analysis: DLS shows the particles to be monodisperse with 135 nm diameter. TEM shows the particles to be approximately spherical of 150 nm diameter.

TGA analysis shows loss of 80.63%, corresponding to the organic material. Elemental analysis shows 68.46% from C, H, N.

Variation of the reagent quantities (examples A4, A5 and A6) in this reaction leads to particles with different particle sizes, as determined by DLS; results are compiled in the below table:

| Example | Compound 2 | Ethanol | Ammonia | Particle size (DLS) |
|---------|-----------|---------|---------|---------------------|
| A4 | 1.0 g | 8.46 ml | 0.507 g | 165 nm |
| A5 | 1.0 g | 4.84 ml | 0.242 g | 125 nm |
| A6 | 3.0 g | 30 ml | 3.0 ml | 310 nm |

Example A7

A mixture of (3-aminopropyl)triethoxysilane (12.46 g), compound 1 (15 g) and ethanol (200 ml) is heated to reflux overnight. The mixture is then cooled to room temperature and ammonium hydroxide (25 ml, 25% aqueous solution) is added. The mixture is stirred overnight at room temperature, then acetone (200 ml) is added and the resulting precipitate filtered off and washed with more acetone followed by diethyl ether. This gives the product as a very dark red solid (11.67 g). DLS shows monodisperse particles with of 41 nm diameter.

Example A8

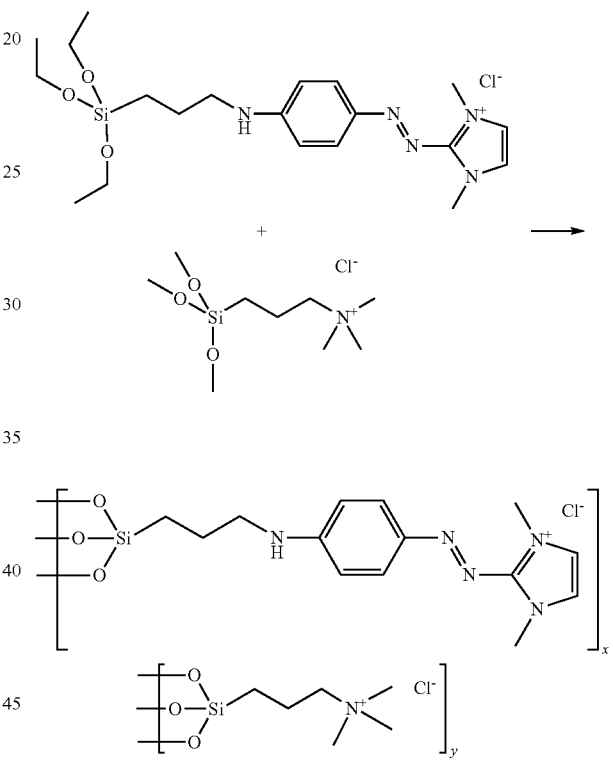

A mixture of compound 2 (1.0 g; 2.2 mmol), N-trimethoxysilylpropyl-N,N,N-trimethylammonium chloride (2.0 g of a 50% solution in methanol [3.9 mmol]), ammonium hydroxide (2.0 ml, 25% solution in water) and ethanol (20 ml) is stirred overnight at room temperature. A large excess of acetone is then added and the formed precipitate filtered and washed with more acetone followed by diethyl ether. This gives the cationic copolymer particle as a dark red solid.

Analytics: DLS shows monodisperse particles with ~280 nm diameter. TGA shows loss of 73.29%, corresponding to the organic material. Elemental analysis shows 54.68% from C, H, N.

Example A9

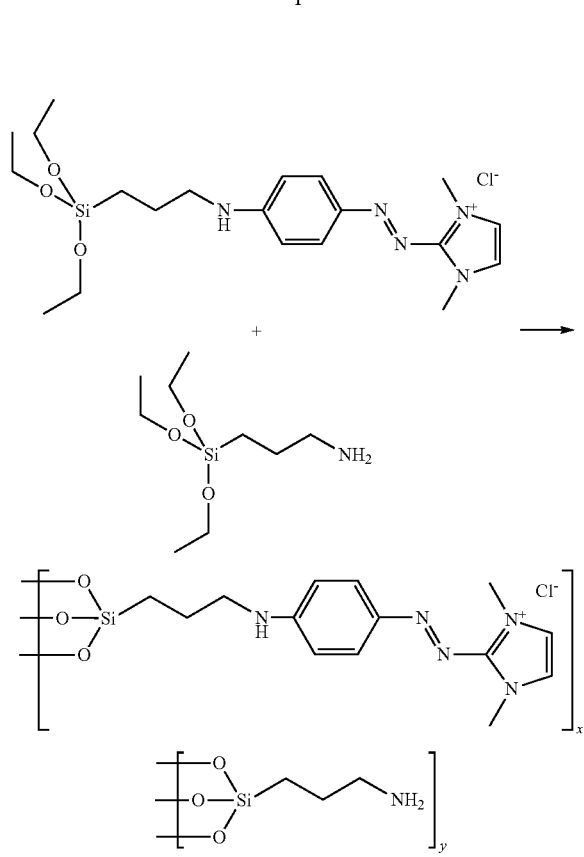

A mixture of compound 2 (0.394 g; 0.86 mmol), (3-aminopropyl)triethoxysilane (1.72 g; 7.77 mmol), ammonium hydroxide (0.89 g, 25% solution in water) and ethanol (26.5 ml) is stirred at room temperature overnight. The solvents are then removed under vacuum, and the residue is triturated with diethyl ether. Filtration of the red solid followed by washing with more diethyl ether gives the product as a dark red solid.

Analytics: DLS shows monodisperse particles with ~350 nm diameter. TGA shows loss of 79.82%, corresponding to the organic material. Elemental analysis shows 50.16% C, H, N.

Example A10

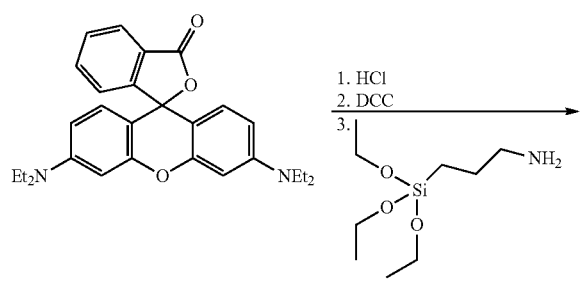

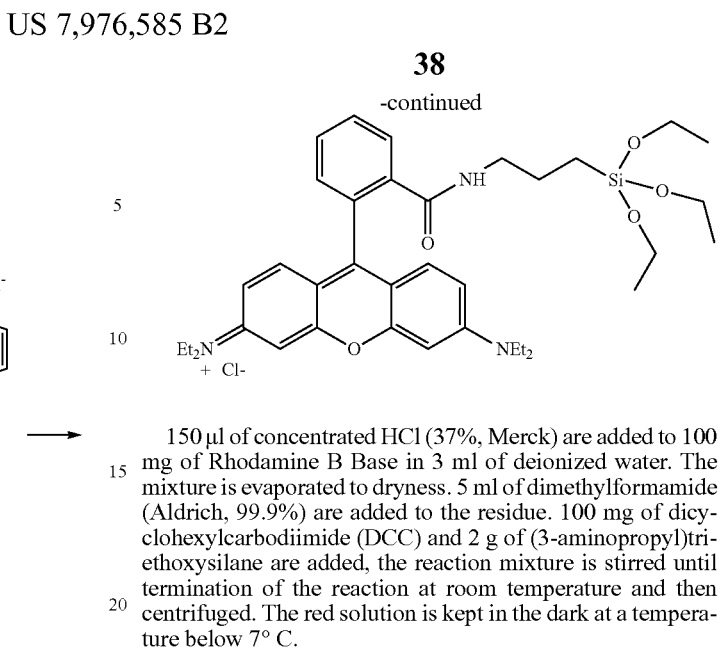

150 μl of concentrated HCl (37%, Merck) are added to 100 mg of Rhodamine B Base in 3 ml of deionized water. The mixture is evaporated to dryness. 5 ml of dimethylformamide (Aldrich, 99.9%) are added to the residue. 100 mg of dicyclohexylcarbodiimide (DCC) and 2 g of (3-aminopropyl)triethoxysilane are added, the reaction mixture is stirred until termination of the reaction at room temperature and then centrifuged. The red solution is kept in the dark at a temperature below 7° C.

Example A11

Alumina Core-Shell Particles

To 10 mg of the fluorescent dye compound of example A10 described above, 200 ml of ethanol and 30 g of 25% aqueous ammonia solution are added under vigorous stirring. The modified "Stöber Process" is carried out during 24 h at room temperature under protection from light. After forming the seed particles (rhodamine rich nucleus), 10 g of aluminium tri-isopropoxid (Aldrich, 99.99%) dissolved in 150 ml of 2-propanol (Aldrich, 99.9%) are added to form the alumina shell. The mixture is stirred for additional 24 h and the nucleus/shell particles are centrifuged. The residue is dispersed in ethanol, precipitated by addition of ethyl acetate, washed and centrifuged thrice until no starting material or unreacted compounds are found in supernatant. The residue is re-dispersed in ethanol until further use.

A sample is dried 24 h in an oven under reduced pressure (70 hPa) at 60° C. and tested in a PVC-foil application. No migration is observed (method: DIN 53775-3).

Example A12

Extended Alumina-Core Particles

The synthesis of extended alumina-core particles is carried out as described above (example 11), but 4 h after start of modified "Stöber Process" with Rhodamine B derivative, 10 g of aluminium tri-isopropoxid (Aldrich, 99.99%) dissolved in 150 ml of 2-propanol (Aldrich, 99.9%) are added under vigorous stirring. The mixture is stirred for additional 24 h and the extended alumina-core particles are centrifuged. The residue is dispersed in ethanol, precipitated by addition of ethyl acetate, washed and centrifuged thrice until no starting material or unreacted compounds are found in supernatant. The residue is re-dispersed in ethanol until further use.

A sample is dried 24 h in an oven under reduced pressure (70 hPa) at a temperature of 60° C. and tested in a PVC-foil application. No migration is observed.

Example A13

Extended Alumina-Core-Shell Particles

The synthesis of extended alumina-core-shell particles is carried out as described above (examples A11/A12), except that 4 h after start of the modified "Stöber Process" with fluorescent Rhodamine B derivative, 5 g of aluminium tri-isopropoxid (Aldrich, 99.99%) dissolved in 100 ml of 2-propanol (Aldrich, 99.9%) are added. The mixture is stirred for additional 24 h at room temperature, then 5 g of aluminium tri-isopropoxid (Aldrich, 99.99%) dissolved in 100 ml of 2-propanol (Aldrich, 99.9%) are added to the vigorously stirred solution. The mixture is stirred for additional 24 h at room temperature and the extended Alumina-core-shell particles are centrifuged. The residue is dispersed in ethanol, precipitated by addition of ethyl acetate, washed and centrifuged thrice until no starting material or unreacted compounds are found in supernatant. The residue is re-dispersed in ethanol until further use. A sample is dried 24 h in an oven under reduced pressure (70 hPa) at a temperature of 60° C. and tested in a 1% PVC-foil application. No migration was observed.

Example A14

Alumina Core-Shell Particles

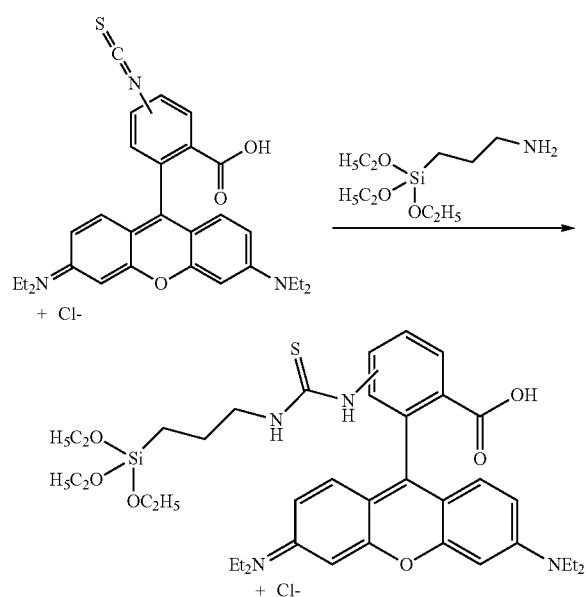

100 mg of Tetraethylrhodamine isothiocyanate is stirred in 40 ml of ethanol (99.9% Aldrich) with 2 g of 3-aminopropyltriethoxysilane for 48 h at room temperature under protection from light.

To 10 mg of the fluorescent dye compound as described above, 200 ml of ethanol and 30 g of 25% aqueous ammonia solution are added under vigorous stirring. The modified "Stöber Process" is carried out during 24 h at room temperature under protection from light. After forming the seed particles (rhodamine rich nucleus), 15 g of aluminium tri-isopropoxid (Aldrich, 99.99%) dissolved in 200 ml of 2-propanol (Aldrich, 99.9%) are added to form the alumina shell. The mixture is stirred for additional 24 h and the alumina-shell particles are centrifuged. The residue is dispersed in ethanol, precipitated by addition of ethyl acetate, washed and centrifuged thrice until no starting material or unreacted compounds are found in supernatant. The residue is re-dispersed in ethanol until further use.

A sample is dried 24 h in an oven under reduced pressure (70 hPa) at a temperature of 60° C. and tested in a 1% PVC-foil application. No migration is observed.

Example A15

Extended Alumina-Core Particles

The synthesis of extended alumina-core particles is carried out as described above (example A14), but 4 h after start of modified "Stöber Process" with TRITC Rhodamine derivative, 10 g of aluminium tri-isopropoxid (Aldrich, 99.99%) dissolved in 150 ml of 2-propanol (Aldrich, 99.9%) are added under vigorous stirring. The mixture is stirred for additional 24 h and the extended alumina-core particles are centrifuged. The residue is dispersed in ethanol, precipitated by addition of ethyl acetate, washed and centrifuged thrice until no starting material or unreacted compounds are found in supernatant. The residue is re-dispersed in ethanol until further use.

A sample is dried 24 h in an oven under reduced pressure (70 hPa) at a temperature of 60° C. and tested in a PVC-foil application. No migration is observed.

Example A16

Extended Alumina-Core-Shell Particles

The synthesis of extended alumina-core-shell particles is carried out as described above (examples A14/A15), but 4 h after start of modified "Stöber Process" with TRITC Rhodamine derivative, 5 g of aluminium tri-isopropoxid (Aldrich, 99.99%) dissolved in 100 ml of 2-propanol (Aldrich, 99.9%) are added under vigorous stirring. The mixture is stirred for additional 24 h at room temperature, then 5 g of aluminium tri-isopropoxid (Aldrich, 99.99%) dissolved in 100 ml of 2-propanol (Aldrich, 99.9%) are added under vigorously stirring. The mixture is stirred for additional 24 h at room temperature and the extended Alumina-core-shell particles are centrifuged. The residue is dispersed in ethanol, precipitated by addition of ethyl acetate, washed and centrifuged thrice until no starting material or unreacted compounds are found in supernatant. The residue is re-dispersed in ethanol until further use.

A sample is dried 24 h in an oven under reduced pressure (70 hPa) at a temperature of 60° C. and tested in a 1% PVC-foil application. No migration is observed.

Example A17

Preparation of Silylated Dye Monomers

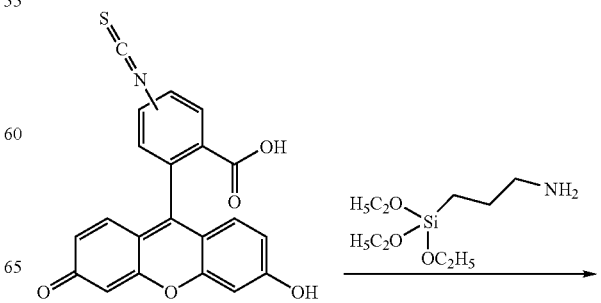

41

-continued

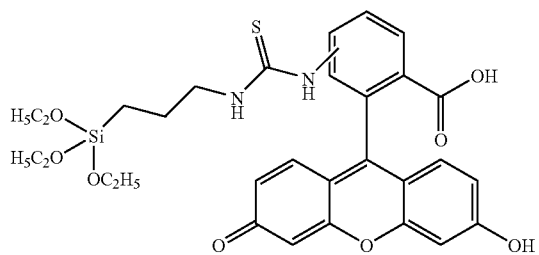

5 mg of Fluorescein isothiocyanate (FITC) is stirred in 4 ml of ethanol (Aldrich, 99.9%) with 100 mg of 3-aminopropyl-triethoxysilane (APTES) for 48 h at room temperature under protection from light.

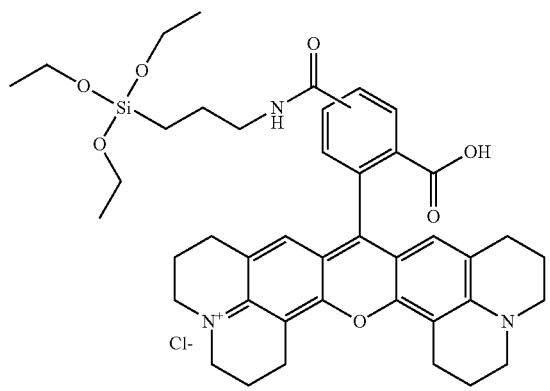

ROX-silane derivative obtainable from:
5-(and-6)-carboxy-X-rhodamine succinimidyl ester

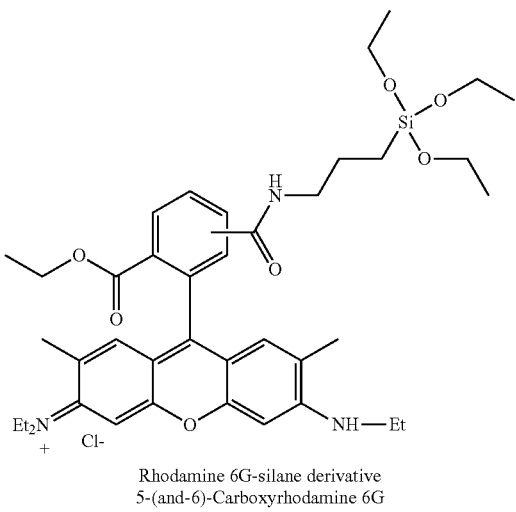

Rhodamine 6G-silane derivative
5-(and-6)-Carboxyrhodamine 6G
Succinimidyl ester 5 mg of 5-(and-6)-carboxyrhodamine 6G succinimidyl ester and 5 mg of 5-(and-6)-carboxy-X-rhodamine succinimidyl ester (R6G-succinimidyl ester and ROX-Succinimidyl ester, each as an isomer mixture, available e.g. from: invitrogen.com) are reacted separately in a similar way as described for Fluoresceine isothiocyanate (FITC) above: each compound is stirred in 5 ml of anhydrous DMF (Aldrich, 99.9%) with 100 mg of 3-aminopropyltriethoxysilane 48 h at room temperature under protection from light.

42

Example A18

Triple-dye-doped Alumina Core-Shell Particles

The mixture of 5 mg of each fluorescent dye compound of "FITC"-silane, "Rh6G"-silane and "ROX"-silane as described above (example A17) is dissolved in 150 ml of ethanol (96% Merck) and the solution added to a mixture of 150 ml of ethanol, 30 g of 25% of ammonia and 100 ml of water under vigorous stirring. The modified "Stöber Process" is carried out during 24 h at room temperature under protection from light. After forming the seed particles (derivatives of R6G/FITC/ROX), 15 g of aluminum tri-isopropoxid (Aldrich, 99.99%) dissolved in 100 ml of 2-propanol (Aldrich, 99.9%) is added to form the alumina shell.

After additional 24 h stirring at room temperature, the alumina core-shell particles are centrifuged. The residue is dispersed in ethanol, precipitated by addition of ethyl acetate, washed and centrifuged thrice until no starting material or unreacted compounds are found in supernatant. The residue is re-dispersed in ethanol until further use.

A sample is dried 24 h in an oven under reduced pressure (70 hPa) at a temperature of 60° C. and tested in a 1% PVC-foil application. No migration is observed.

Example A19

Extended Alumina-Core-Particles

The synthesis of extended core particles is carried out as described above (example A18), but 4 h after start of modified "Stöber Process" with R6G/FITC/ROX derivatives, 15 g of aluminum tri-isopropoxid (Aldrich, 99.99%) dissolved in 200 ml of 2-propanol (Aldrich, 99.9%) are added under vigorous stirring. The mixture is stirred for additional 24 h at room temperature and the extended alumina-core particles are centrifuged. The residue is dispersed in ethanol, precipitated by addition of ethyl acetate, washed and centrifuged thrice until no starting material or unreacted compounds are found in supernatant. The residue is re-dispersed in ethanol until further use.

A sample is dried 24 h in an oven under reduced pressure (70 hPa) at a temperature of 60° C. and tested in a 1% PVC-foil application. No migration is observed.

Example A20

Extended Alumina-Core-Shell Particles

The synthesis of extended core-shell particles is carried out as described above (examples A18/A19), but 4 h after start of modified "Stöber Process" with R6G/FITC/ROX derivatives, 7.5 g of aluminum tri-isopropoxid (Aldrich, 99.99%) dissolved in 100 ml of 2-propanol (Aldrich, 99.9%) are added to the vigorously stirred solution. The mixture is stirred for additional 24 h at room temperature, then 7.5 g of aluminum tri-isopropoxid (Aldrich, 99.99%) dissolved in 100 ml of 2-propanol (Aldrich, 99.9%) are added under vigorously stirring. The mixture is stirred for additional 24 h at room temperature and the alumina extended core-shell particles are centrifuged. The residue is dispersed in ethanol, precipitated by addition of ethyl acetate, washed and centrifuged thrice until no starting material or unreacted compounds are found in supernatant. The residue is re-dispersed in ethanol until further use.

A sample is dried 24 h in an oven under reduced pressure (70 hPa) at a temperature of 60° C. and tested in a 1% PVC-foil application. No migration is observed.

Example A21

Preparation of Silylated Dye Monomers

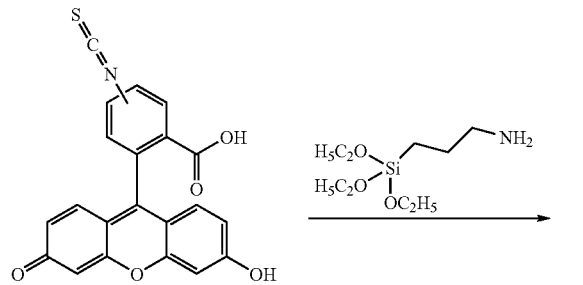

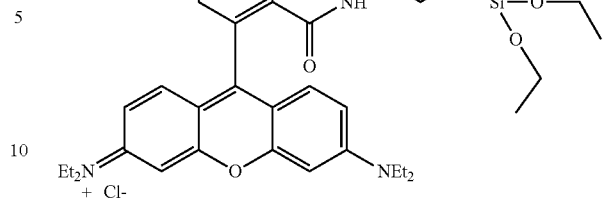

Similarly as in Example A17, 5 mg of Fluoresceine isothiocyanate (FITC) is stirred in 4 ml of ethanol (99.9% Aldrich) with 100 mg of 3-aminopropyltriethoxysilane (APTES) and 50 mg of propyltrimethoxysilane (PS) for 48 h under protection from light at room temperature.

In a similar manner are prepared:

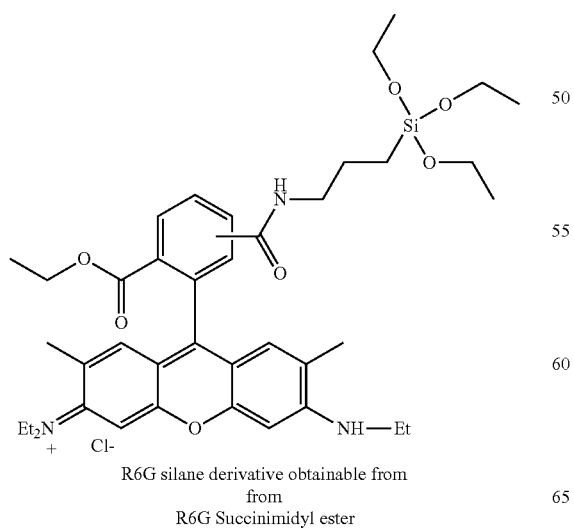

R6G silane derivative obtainable from
from
R6G Succinimidyl ester

-continued

Rhodamine silane derivative obtainable
Rhodamine B (DCC-method)

10 mg of R6G-succinimidyl ester and 10 mg of Rhodamine B (DCC-method, see example A17) are reacted separately as described for Fluoresceine isothiocyanate (FITC): each compound was stirred in 5 ml of anhydrous DMF (Aldrich, 99.9%) with 250 mg of 3-aminopropyltriethoxysilane (APTES) and 50 mg of propyltrimethoxysilane (PS) 48 h at room temperature under protection from light.

Example A22

Silica Core-Shell Particles

The mixture of 10 mg of each fluorescent dye compound of "FITC"-silane, "Rhodamine 6G"-silane and "Rhodamine B"-silane as described above is dissolved in 150 ml of ethanol (96% Merck) and the solution is added to a mixture of 200 ml of ethanol (96%, Merck), 30 g of 25% of ammonia and 100 ml of water under vigorous stirring. The modified "Stöber Process" is carried out during 24 h at room temperature under protection from light. After forming the seed particles (derivatives of R6G/FITC/Rhd B), 25 g of tetraethoxysilane (TEOS) dissolved in 100 ml of ethanol are added to form the silica shell. The mixture is stirred for additional 24 h and the core-shell particles are centrifuged. The residue is dispersed in ethanol, precipitated by addition of ethyl acetate, washed and centrifuged thrice until no starting material or unreacted compounds are found in supernatant. The residue is re-dispersed in ethanol until further use.

A sample is dried 24 h in an oven under reduced pressure (70 hPa) at a temperature of 60° C. and tested in a 1% PVC-foil application. No migration is observed.

Example A23

Extended Silica-Core-Particles

The synthesis of extended core particles is carried out as described above (example A22), but 4 h after start of modified "Stöber Process" with derivatives of R6G/FITC/Rhd B, 25 g of tetraethoxysilane dissolved in 150 ml of ethanol is added to the vigorously stirred solution. The mixture is stirred for additional 24 h at room temperature, and the silica extended core particles are centrifuged. The residue is dispersed in ethanol, precipitated by addition of ethyl acetate, washed and centrifuged thrice until no starting material or unreacted compounds are found in supernatant. The residue is re-dispersed in ethanol until further use.

A sample is dried 24 h in an oven under reduced pressure (70 hPa) at a temperature of 60° C. and tested in a 1% PVC-foil application. No migration is observed.

Example A24
Hair Dye Red Seed-particles
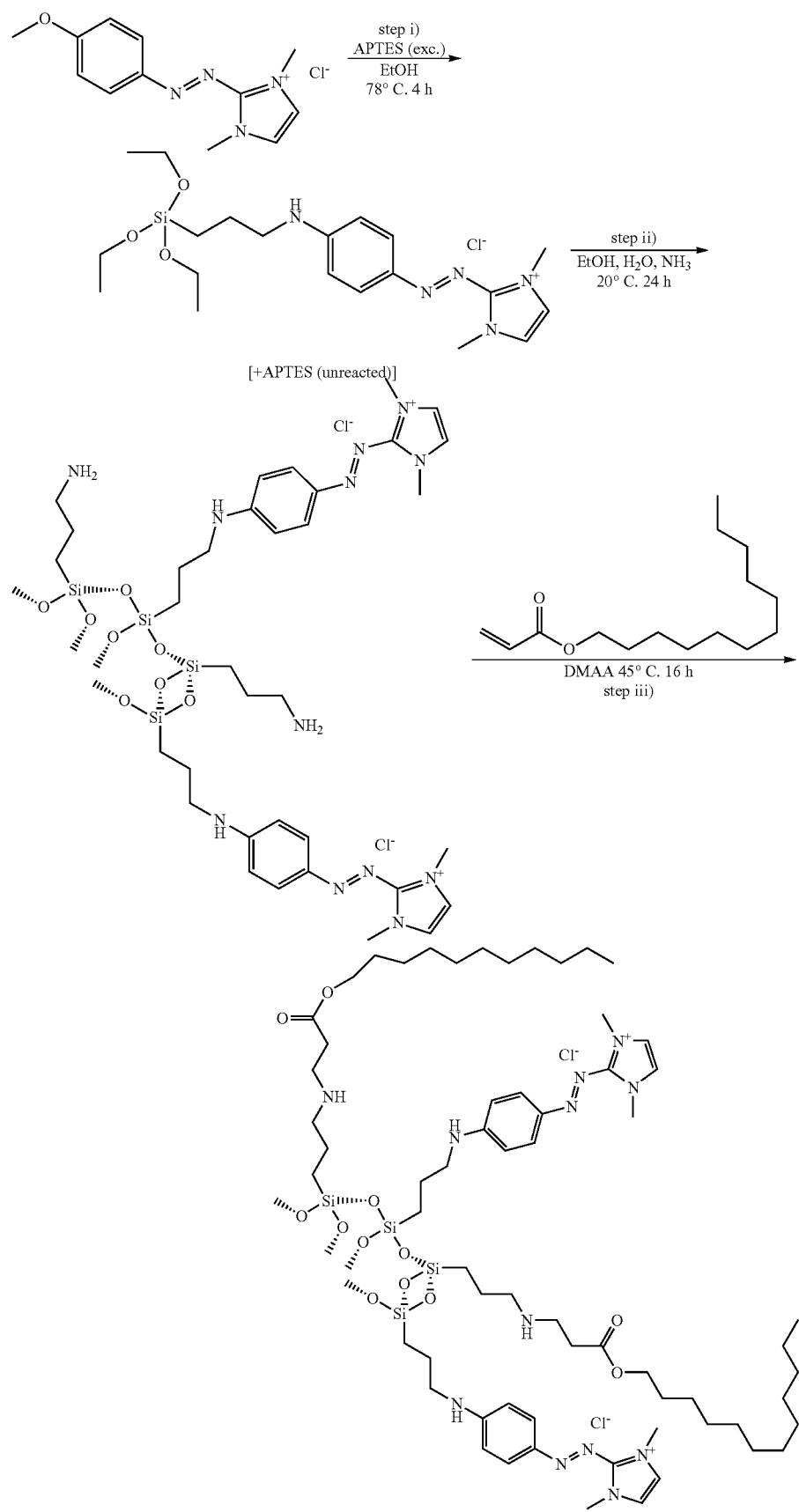

i) 0.75 g of Hair-Dye Red are dissolved in 70 ml of anhydrous ethanol, a mixture of 2.9 g of 3-aminopropyltriethoxysilane (APTES) in 20 ml of ethanol is added to the orange solution and heated at 78° C.

ii) After 4 h, the dark red solution is cooled to room temperature and introduced into a modified "Stöber Process". The reaction medium, consisting of 150 ml ethanol, 50 ml of water and 30 g of 25% aqueous ammonia solution, is stirred vigorously for 24 h at room temperature. After forming the seed particles, 50% of the solvent is evaporated in a rotary evaporator under reduced pressure. The residue is mixed with 200 ml of ethyl acetate, centrifuged and the obtained residue washed and centrifuged thrice with ethyl acetate until no starting material or unreacted compounds are found in supernatant.

iii) The dark red colored residue is dispersed in 50 ml of dimethylacetamide, combined with 15 g of dodecylacrylate (Aldrich, techn. 90%) and stirred for 16 h at a temperature of 45° C. The mixture is diluted with 100 ml of ethyl acetate, washed and centrifuged thrice until no starting material or unreacted compounds are found in supernatant. After evaporation of the solvent, the residue is dispersed in dodecane (1% particle content w/w) for electrophoretic color-filter application; analytical results obtained from measurements with MALVERN Zeta-Sizer® are shown in the below table:

| Example A24 | Data (20° C. in dodecane) |
| --- | --- |
| Zeta-Potential: | −42.1 mV |
| Mobility: | 0.0362 m$^2$/Vsx10$^{-8}$ |
| Particle size (DLS): | 7 nm |

Example A25

Extended Silica-Seed-Particles

The synthesis of extended silica-seed particles is carried out as described above (example A24), but 4 h after start of modified "Stöber Process" with Hair-Dye Red-silane derivative, 0.3 g of tetraethoxysilane (Aldrich, 99.99%), dissolved in 20 ml of 2-propanol, is added to the vigorously stirred solution. The mixture is stirred for additional 24 h at room temperature and the extended silica-seed particles are centrifuged. The residue is dispersed in ethyl acetate, washed and centrifuged thrice until no starting material or unreacted compounds are found in supernatant. The residue is stored in ethyl acetate until further processing.

A sample is dried 24 h in an oven under reduced pressure (70 hPa) at a temperature of 60° C. and tested in a PVC-foil application. No migration is observed.

Example A26

Victoria Blue Seed-particles i) Deprotonating Victoria Blue 51.52 g of C.I. Basic Blue 7 are dissolved in 750 ml of distilled water and then, under stirring, a 2N solution of sodium hydroxide in water is added dropwise until the deprotonated form of the dye has completely precipitated, no blue colour remains in the solution and does not return for several hours. The precipitate is filtered off, washed with distilled and decarbonated water until the filtrate is free of chloride ions, and dried at 60° C. under reduced pressure (200 mbar). 45.23 g (94.7%) of the deprotonated C.I. Basic Blue 7 are isolated as a nearly black powder.

ii) Modification of Iodopropyl(trimethoxy)silane to -triethoxysilane Derivative

A solution of 2.0 ml (2.95 g; 10.2 mmol) of 3-iodopropyl-trimethoxysilane in 50 ml of anhydrous ethanol is stirred at ambient temperature under argon for 60 hours, and subsequently the solvent is distilled off under reduced pressure, resulting in complete exchange of the methoxy by ethoxy groups.

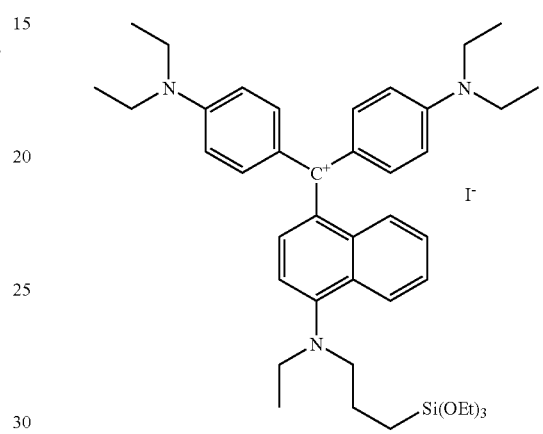

iii) Coupling of Compounds

The residue is dissolved in 50 ml of anhydrous acetonitrile, 2.389 g (5 mmol) of deprotonated C.I. Basic Blue 7 are added, and the solution is heated under argon under reflux for 24 hours. The solvent is distilled off, and the semi-solid residue is washed several times with methyl-tert-butylether in order to remove the excess of the alkylating agent and unreacted deprotonated dye, until the filtrate is nearly colourless, avoiding the intrusion of atmospheric moisture during the procedure. Without drying, the solid residue is dissolved in 50 ml of anhydrous ethanol.

iv) Stöber-Process 1 g of silanized Victoria Blue dissolved in 25 ml of ethanol was introduced into a reaction medium consisting of 150 ml of ethanol (96%), 50 ml of water and 30 g of 25% aqueous ammonia solution with vigorous stirring for 24 h at room temperature. After forming the seed particles (dye rich nucleus), the mixture is centrifuged. The residue is dispersed in ethanol (80%), washed and centrifuged thrice until no starting material or unreacted compounds are found in supernatant.

The residue is dispersed in 20 ml of DMSO, stirred in 400 ml of deionized water and precipitated by addition of:

a) 4 g of Ammonium molybdate tetrahydrate $(NH_4)_6Mo_7O_{24} \cdot 4H_2O$ (Fluka, puriss) in 30 ml of water or b) 6 g of Ammonium phosphomolybdate hydrate $(NH_4)_3Mo_{12}O_{40} \cdot xH_2O$ (Aldrich) in 30 ml of water.

The precipitates contain the following species:

(a)
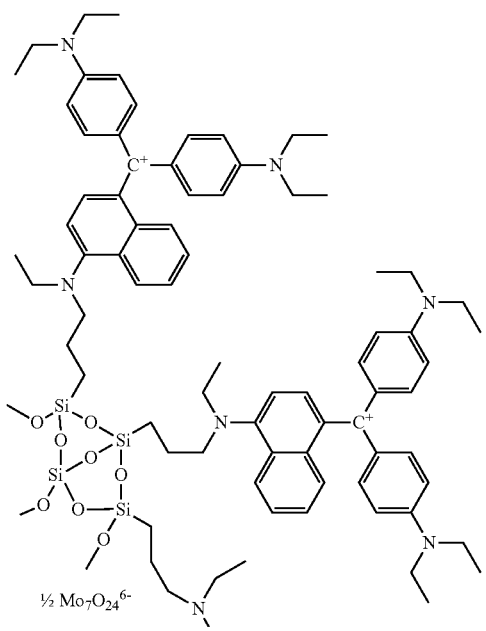
½ Mo₇O₂₄⁶⁻

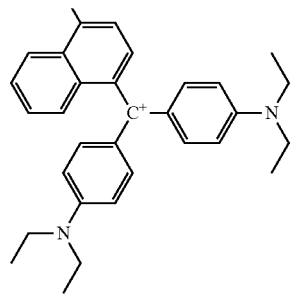

(b)
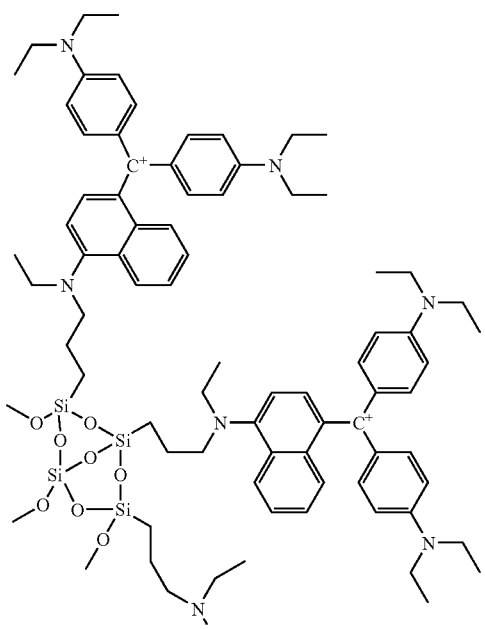

PMo₁₂O₄₀³⁻
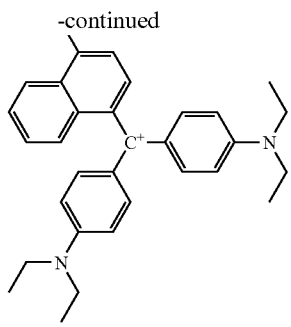

The precipitate is filtered off, washed with acetone and dried.

Example A27

Extended Silica-Core-particles

The synthesis of extended core particles is carried out as described above (example A26), but 4 h after start of modified "Stöber Process" with Victoria Blue silane derivative, 0.4 g of tetraethoxysilane (Aldrich, 99.99%) dissolved in 20 ml of ethanol are added to the vigorously stirred solution. The mixture is stirred for additional 24 h at room temperature, and the silica extended core particles are centrifuged. The residue is dispersed in ethanol, precipitated by addition of ethyl acetate, washed and centrifuged thrice until no starting material or unreacted compounds are found in supernatant. The residue is dispersed in 20 ml of DMSO, stirred in 400 ml of deionized water and precipitated by addition of 4 g of Ammonium molybdate $(NH_4)_6Mo_7O_{24} \times 4H_2O$ (Fluka, puriss) in 30 ml of water. The residue is dispersed in 20 ml of DMSO, stirred in 400 ml of deionized water and precipitated by addition of:

a) 4 g of Ammonium molybdate tetrahydrate $(NH_4)_6Mo_7O_{24} \times 4H_2O$ (Fluka, puriss) in 30 ml of water b) 6 g of Ammonium phosphomolybdate hydrate $(NH_4)_3Mo_{12}O_{40} \times H_2O$ (Aldrich) in 30 ml of water 1/6 Mo₇O₂₄⁶⁻

-continued

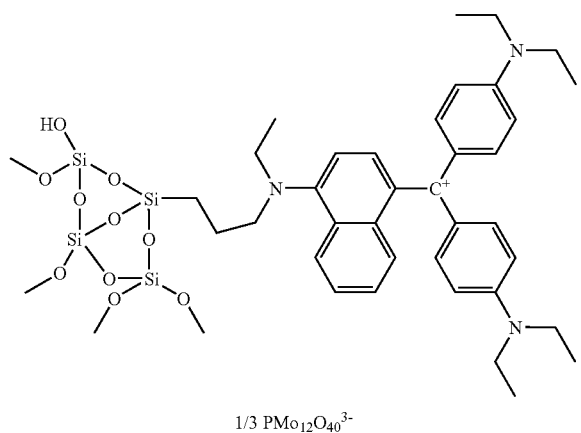

1/3 PMo$_{12}$O$_{40}$$^{3-}$

The precipitate was filtered off, washed with acetone and dried.

B. Application Testing

The washing fastness of the dyed hair is analyzed using the Gray scale according to: *Industrial Organic Pigments*, Herbst & Hunger, 2nd ed. engl. p. 61, no. 10: DIN 54001-8-1982, "*Herstellung and Bewertung der Änderung der Farbe*", ISO 105-A02-1993.

Example B1

50 mg of the compound obtained in example A2, is dispersed in 50 g water. This red dyeing agent is applied on the dry hair (two blond, two middle blond and two damaged hair strands) and allowed to stand for 20 min. at room temperature. Then, the strands are rinsed under tap water and dried for 12 hours.

Washing fastness: 10× washed with shampoo.
Results:

| Strand | Color Result | Washing Fastness |
|---|---|---|
| blond | Red/good | 3-4 |
| middleblond | Red/good | 4 |
| damaged | Red/good | 4 |

Example B2

First 100 g Plantacare 200UP (ID: 185971.5) are filled up to 1000 g with H$_2$O dest. (=10 wt. %). The pH is adjusted to 9.5 with 50% citric acid solution or monoethanolamine solution. Then 50 mg of the compound obtained in example A2, is dispersed in 50 g of the Plantacare solution. This red dyeing agent is applied on the dry hair (two blond, two middle blond and two damaged hair strands) and allowed to stand for 20 min. at room temperature. Then, the strands are rinsed under tap water and dried for 12 hours.

Washing fastness: 10× washed with shampoo.
Results:

| Strand | Color Result | Washing Fastness |
|---|---|---|
| blond | Red/good | 4 |
| middleblond | Red/good | 4 |
| damaged | Red/good | 3-4 |

Example B3

50 mg of the compound obtained in example A3, is dispersed in 50 g water. This red dyeing agent is applied on the dry hair (two blond, two middle blond and two damaged hair strands) and allowed to stand for 20 min. at room temperature. Then, the strands are rinsed under tap water and dried for 12 hours.

Washing fastness: 10× washed with shampoo.
Results:

| Strand | Color Result | Washing Fastness |
|---|---|---|
| blond | Red/good | 4 |
| middleblond | Red/good | 4-5 |
| damaged | Red/good | 3-4 |

Example B4

50 mg of the compound obtained in example A5, is dispersed in 50 g water and the pH value is adjusted to 9.8 with NaOH. This red dyeing agent is applied on the dry hair (two blond, two middle blond and two damaged hair strands) and allowed to stand for 20 min. at room temperature. Then, the strands are rinsed under tap water and dried for 12 hours.

Washing fastness: 10× washed with shampoo.
Results:

| Strand | Color Result | Washing Fastness |
|---|---|---|
| blond | Red/good | 4 |
| middleblond | Red/good | 4-5 |
| damaged | Red/good | 3 |

Example B5

50 mg of the compound obtained in example A6, is dispersed in 50 g water and the pH value is adjusted to 9.4 with NaOH. This red dyeing agent is applied on the dry hair (two blond, two middle blond and two damaged hair strands) and allowed to stand for 20 min. at room temperature. Then, the strands are rinsed under tap water and dried for 12 hours.

Washing fastness: 10× washed with shampoo.
Results:

| Strand | Color Result | Washing Fastness |
|---|---|---|
| blond | Red/good | 4 |
| middleblond | Red/good | 3 |
| damaged | Red/good | 3 |

Example B6

50 mg of the compound obtained in example A8, is dispersed in 50 g water and the pH value is adjusted to 9.8 with NaOH. This red dyeing agent is applied on the dry hair (two blond, two middle blond and two damaged hair strands) and allowed to stand for 20 min. at room temperature. Then, the strands are rinsed under tap water and dried for 12 hours.

Washing fastness: 10× washed with shampoo.
Results:

| Strand | Color Result | Washing Fastness |
|---|---|---|
| blond | Red/good | 4-5 |
| middleblond | Red/good | 4 |
| damaged | Red/good | 2-3 |

In the following application examples compositions within the below given definitions are used:

Example B7

A tress of blond hair is shampooed with a shampoo, containing 0.03% of the dye A7 and

| | |
|---|---|
| Disodium PEG-5 Laurylcitrate Sulfosuccinate, Sodium Laureth Sulfate | 8.25 wt. % |
| Sodium Cocoamphoacetate | 20.9 wt. % |
| Methoxy PEG/PPG-7/3 Aminopropyl Dimethicone | 0.5 wt. % |
| Hydroxypropyl Guar hydroxypropyltrimonium Chloride | 0.3 wt. % |
| PEG-200 Hydrogenated Glyceryl Palmate; PEG-7 Glyceryl Cocoate | 2.5 wt. % |
| PEG-150 Distearate | 0.5 wt. % |
| Citric Acid (30%) | 2.2 wt. % |
| Perfume; Preservatives | q.s. |
| Water (final pH of 5.4) | Ad 100 wt. % |

After 5 minutes at RT the tress is rinsed with warm water and dried. The tress has been dyed red. After repeating this procedure 5 times the colour result is intensified.

Example B8

A conditioner containing 0.02% of the dye A7 and

| | |
|---|---|
| Cetyl Alcohol | 3.00 wt. % |
| Cetereareth-25 | 0.50 wt. % |
| Distearyldimonium Chloride | 1.00 wt. % |
| Quaternium-80 | 0.50 wt. % |
| Citric Acid | Ad pH = 5 |
| Perfumes; Preservatives | q.s. |
| Water | Ad 100 wt. % | is applied to a tress of shampooed middle blond hair at RT. After 20 minutes the tress is rinsed and dried. The tress has been dyed intensive red.

Example B9

1% of compound A7 is dissolved in a 5% solution of a non-ionic surfactant (Plantacare 200UP, Henkel) adjusted to pH 9.5 using citric acid or monoethanolamine. Then 1% Natrosol is added and this solution is stirred for 30 min. The thickened dyeing solution is applied on dry blond, middle blond and damaged hair strands and allowed to stand for 20 min. at room temperature. Then, the strands are rinsed under tap water and dried 12 hours. The tresses have been dyed intensive red.

Example B10

The dyeing formulation of application example B9 is mixed with 1 weight of 6% hydrogen peroxide solution and the mixture is immediately applied to a tress of brown hair. After 30 minutes the tress is rinsed, shampooed, rinsed and dried. The tress has been dyed intensively red.

Example B11

A dye emulsion, containing 1% of the dye A7 and

| | |
|---|---|
| Oleth-5 | 6.0 wt. % |
| Oleic acid | 6.0 wt. % |
| Stearic acid monoethanolamide | 4.0 wt. % |
| Coco fatty acid monoethanolamide | 4.0 wt. % |
| 1,2-Propanediol | 1.0 wt. % |
| Ammoniumchloride | 0.5 wt. % |
| EDTA, Tetrasodiumsalt | 0.2 wt. % |
| Silica | 0.1 wt. % |
| Water | ad 100 wt. % |
| Ammonia | ad pH 10 | is applied to a tress of middle blond hair at RT. After 30 minutes the tress is rinsed, shampooed, rinsed and dried. The tress has been dyed intensively red.

Example B12

The dye emulsion of example B11 is mixed with the same weight of 6% hydrogen peroxide solution. This mixture is immediately applied to a tress of blond hair at room temperature. After 30 minutes the tress is rinsed, shampooed, rinsed and dried. The tress has been dyed red.

The invention claimed is:

1. A highly crosslinked polysiloxane dye comprising at least 10 Si atoms, including at least one moiety of the formula (I)

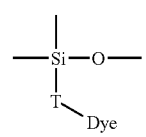

whose open Si-bonds each are linked to an oxygen atom and open O-bond is linked to a silicon atom in the rest of the polysiloxane, and wherein T is a direct bond or an organic spacer group such as $C_1$-$C_{18}$alkylene, $C_2$-$C_{12}$alkenylene, $C_5$-$C_{10}$cycloalkylene, $C_5$-$C_{10}$arylene, —$C_5$-$C_{10}$arylene-($C_1$-$C_{10}$alkylene)-, each of which may be end-capped towards the linkage to Dye by CO, COO, $NR^1$, $CONR^1$, $NR^1CONR^1$, CS, CSS, $CSNR^1$, $NR^1CSNR^1$, O, S, SO, $SO_2$, $C_5$-$C_{10}$cycloalkylene, $C_5$-$C_{10}$arylene; or T is $C_3$-$C_{18}$alkylene interrupted, and optionally end-capped towards the linkage to Dye, by CO, COO, $NR^1$, $CONR^1$, $NR^1CONR^1$, CS, CSS, $CSNR^1$, $NR^1CSNR^1$, O, S, SO, —$SO_2$—, $C_5$-$C_{10}$cycloalkylene, $C_5$-$C_{10}$arylene; or is CO; $(CH_2CH_2$—$O)_{1-5}$; COO; $N(R^1)$; $CON(R^1)$; O; S; SO; $SO_2$;

$R^1$ is hydrogen; unsubstituted or substituted, straight-chain or branched, monocyclic or polycyclic, interrupted or uninterrupted $C_1$-$C_{14}$alkyl; $C_2$-$C_{14}$alkenyl; $C_6$-$C_{10}$aryl; $C_6$-$C_{10}$aryl-$C_1$-$C_{10}$alkyl; or $C_5$-$C_{10}$alkyl($C_5$-$C_{10}$aryl); and Dye is a residue of an organic dye.

2. A polysiloxane dye according to claim 1, which is represented by the formula (II)

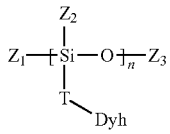

(II)

wherein T is as defined in claim 1,

Dyh is a residue Dye or a cationic moiety other than the one of an organic dye or is hydrogen;

n equals the number of silicon atoms in the polysiloxane and is a number from 10 to about $10^9$, while at least 3 moieties Dyh in the polysiloxane of formula (II), are a residue Dye;

$Z_1$ and $Z_2$ independently are bonds each linked to an oxygen atom of the rest of the polysiloxane or are OH or alkoxy such as $C_1$-$C_8$alkoxy or halogen;

or $Z_2$ may also be $C_1$-$C_8$alkyl or -T-Dyh;

$Z_3$ is a bond linked to a silicon atom of the rest of the polysiloxane or is OH, alkoxy or halogen;

or $Z_3$ together with one of $Z_1$ or $Z_2$ commonly form the same chemical bond.

3. A polysiloxane dye according to claim 1 in the form of particles whose dimensions, in at least one spatial direction(s) are in the nanoparticle size range from 5 to 1000 nm.

4. A polysiloxane dye according to claim 1 wherein the number of organic dye moieties Dye ranges from 3 to $10^8$, and the total number of Si atoms is at least 30.

5. A polysiloxane dye according to claim 1 wherein the organic dye moietes Dye are selected from cationic dye moieties selected from the group consisting of anthraquinone, acridine, azo, azamethine, hydrazomethine, triphenylmethane, benzodifuranone, coumarine, diketopyrrolopyrrol, dioxazine, diphenylmethane, formazane, indigoid indophenol, naphthalimide, naphthoquinone, nitroaryl, merocyanine, methine oxazine, perinone, perylene, pyrenequinone, phtalocyanine, phenazine, quinoneimine, quinacridone, quinophtalone, styryl, stilbene, xanthene, thiazine and thioxanthene dyes;

whose positive charges are compensated by suitable anions.

6. A polysiloxane dye according to claim 1 wherein the organic dye moietes Dye are selected from those of the formulae

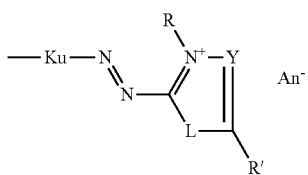

(X)

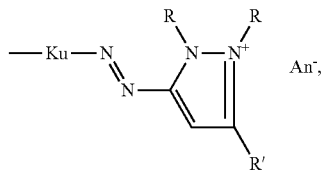

(XI)

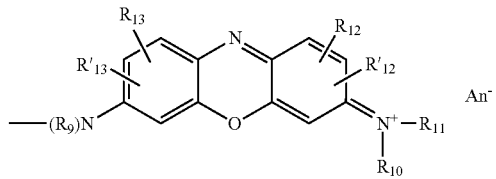

(XII)

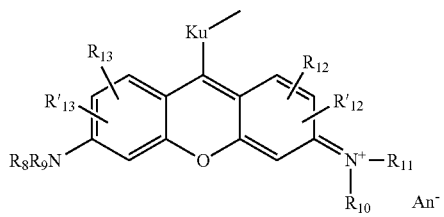

(XIII)

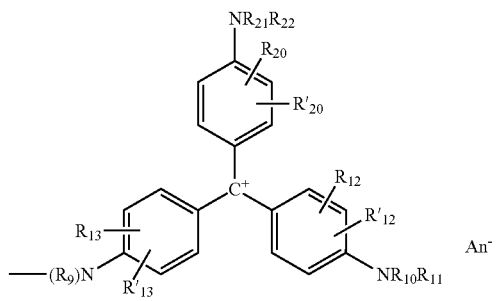

(XIV)

where

An⁻ stands for an equivalent of a colorless anion;

Ku is a divalent radical of a coupling component of the aniline or phenol series or the radical of a heterocyclic coupling component, L is O, S or $NR^1$;

Y is $CR^3$ or N;

R is $C_1$-$C_4$alkyl;

R' is hydrogen, $C_1$-$C_4$alkyl, Cl, nitro, amino, $C_1$-$C_4$nonoalkylamino or di-$C_1$-$C_4$alkylamino;

$R^1$ is H or $C_1$-$C_4$alkyl;

$R^3$ is H, $C_1$-$C_4$alkyl, or $C_1$-$C_4$alkyl substituted by OH—, $C_1$-$C_4$alkoxy-, halogen-, CN—, amino-, $C_1$-$C_4$monoalkylamino- or di-$C_1$-$C_4$alkylamino;

$R_8$, $R_9$, $R_{10}$, $R_{11}$, $R_{21}$ and $R_{22}$ are each independently of the others hydrogen or $C_1$-$C_4$alkyl;

$R_{12}$, $R'_{12}$, $R_{13}$, $R'_{13}$, $R_{20}$ and $R'_{20}$ are each independently of the other hydrogen, $C_1$-$C_4$alkyl or $C_1$-$C_4$alkoxy;

or one or more pairs of residues $R_8$, $R_9$, $R_{13}$, $R'_{13}$; and/or $R_{10}$, $R_{11}$, $R_{12}$, $R'_{12}$; and/or $R_{20}$, $R'_{20}$, $R_{21}$, $R_{22}$, bonding directly to the same phenyl ring or connected via nitrogen to said ring, together with the atoms they are attached to and further intermediary atoms, if present, form an aliphatic or aromatic ring.

7. Process for the preparation of a highly crosslinked polysiloxane dye according to claim 1, wherein a silane reaction mixture comprising a monomer of the formula (III)

$$X_3Si\text{-}T\text{-}Dye \qquad (III),$$

wherein X is a leaving group selected from the group consisting of halogen and alkoxy;

T is a direct bond or an organic spacer group selected from the group consisting of $C_1$-$C_{18}$alkylene, $C_2$-$C_{12}$alkenylene, $C_5$-$C_{10}$cycloalkylene, $C_5$-$C_{10}$arylene and —$C_5$-$C_{10}$arylene-($C_1$-$C_{10}$alkylene)-, each of which may be end-capped towards the linkage to Dye by CO, COO, NR$^1$, CONR$^1$, NR$^1$CONR$^1$, CS, CSS, CSNR$^1$, NR$^1$CSNR$^1$, O, S, SO, —SO$_2$—, $C_5$-$C_{10}$cycloalkylene, $C_5$-$C_{10}$arylene; or T is $C_3$-$C_{18}$alkylene interrupted, and optionally end-capped towards the linkage to Dye, by CO, COO, NR$^1$, CONR$^1$, NR$^1$CONR$^1$, CS, CSS, CSNR$^1$, NR$^1$CSNR$^1$, O, S, SO, —SO$_2$—, $C_5$-$C_{10}$cycloalkylene, $C_5$-$C_{10}$arylene; or is CO—; —(CH$_2$CH$_2$—O)$_{1-5}$—; COO; N(R$^1$); CON(R$^1$); O; S; SO; —SO$_2$—;

R$^1$ is hydrogen; unsubstituted or substituted, straight-chain or branched, monocyclic or polycyclic, interrupted or uninterrupted $C_1$-$C_{14}$alkyl; $C_2$-$C_{14}$alkenyl; $C_6$-$C_{10}$aryl; $C_6$-$C_{10}$aryl-$C_1$-$C_{10}$alkyl; or $C_5$-$C_{10}$alkyl($C_5$-$C_{10}$aryl);

and Dye is a residue of an organic dye, is subjected to polycondensation.

8. Process according to claim 7, wherein the reaction mixture additionally contains one or more further copolymerizable silane monomers of the formulae $$X_3Si\text{-}T\text{-}H \qquad (IIIa),$$

$$X_3Si\text{-}T\text{-}A \qquad (IIIb),$$

$$X_2Si(R^2)\text{-}T\text{-}Dye \qquad (IV)$$

$$X_2Si(R^2)\text{-}T\text{-}H \qquad (IVa),$$

$$X_2Si(R^2)\text{-}T\text{-}A \qquad (IVb),$$

where those monomers containing no radical Dye are contained in an amount of up to 90 mol-% of the total silane monomers in the initial reaction mixture;

and/or one or more of the above monomers of the formulae (IIIa), (IIIb), (IV), (IVa), (IVb), or of the formulae or one or more of the above monomers of the formulae (111a), (IIIb), (IV), (IVa), (IVb), or of the formulae $$X_3Al \qquad (Ia),$$

$$X_4Si \qquad (Ib),$$

$$X_2Al\text{-}T\text{-}H \qquad (IIIc),$$

$$X\text{—}Al(R^2)\text{-}T\text{-}H \qquad (IVc),$$

$$XSi(R^2)_2\text{-}T\text{-}Dye \qquad (V),$$

$$XSi(R^2)_2\text{-}T\text{-}H \qquad (Va),$$

$$XSi(R^2)_2\text{-}T\text{-}A \ (Vb),$$

are added to the reaction mixture after commencement of the polycondensation reaction;

and wherein

A is a cationic moiety other than the one of an organic dye, whose charge is balanced by a suitable anion, R$^2$ is $C_1$-$C_8$alkyl or -T-Dye or -T-H or -T-A.

9. Highly crosslinked polysiloxane dye obtained by a process according to claim 7.

10. A composition comprising at least one polysiloxane dye as defined in claim 1 and a further component selected from synthetic organic polymers, natural organic polymers, cosmetically acceptable carriers, further dyes, oxidative agents and detergents.

11. A composition according to claim 10 comprising in addition at least one single further direct dye and/or an oxidative agent.

12. A composition according to claim 10 in form of a shampoo, a conditioner, a gel or an emulsion.

13. A method of dyeing an organic material, which comprises treating the organic material with at least one dye according to claim 1.

14. A method according to claim 13, wherein the organic material is selected from keratin-containing fibers such as human hair.

15. Compound of one of the formulae

-continued

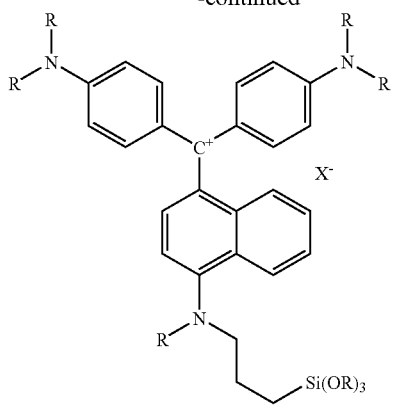

wherein R independently is $C_1$-$C_4$alkyl and $X^-$ stands for an equivalent of a colorless anion.

16. The highly crosslinked polysiloxane dye according to claim 1, wherein the Dye is a cationic organic dye.

17. Highly crosslinked polysiloxane dye obtained by a process according to claim 8.

18. A method of dyeing an organic material, which comprises treating the organic material with at least a composition according claim 10.

19. A method of dyeing an organic material, which comprises treating the organic material with at least a composition according claim 12.

* * * * *